United States Patent
Brownhill et al.

(10) Patent No.: US 11,633,153 B2
(45) Date of Patent: Apr. 25, 2023

(54) POSITIONING OF SENSORS FOR SENSOR ENABLED WOUND MONITORING OR THERAPY

(71) Applicant: Smith & Nephew PLC, Watford (GB)

(72) Inventors: Varuni Rachindra Brownhill, Swanland (GB); Victoria Jody Hammond, Hull (GB); Allan Kenneth Frazer Grugeon Hunt, Beverley (GB); Marcus Damian Phillips, Wakefield (GB); Damian Smith, Swanland (GB); Charlotte Urwin, Hull (GB)

(73) Assignee: Smith & Nephew PLC, Watford (GB)

( * ) Notice: Subject to any disclaimer, the term of this patent is extended or adjusted under 35 U.S.C. 154(b) by 565 days.

(21) Appl. No.: 16/625,279

(22) PCT Filed: Jun. 21, 2018

(86) PCT No.: PCT/EP2018/066569
§ 371 (c)(1),
(2) Date: Dec. 20, 2019

(87) PCT Pub. No.: WO2018/234443
PCT Pub. Date: Dec. 27, 2018

(65) Prior Publication Data
US 2020/0214637 A1    Jul. 9, 2020

Related U.S. Application Data

(60) Provisional application No. 62/524,413, filed on Jun. 23, 2017.

(51) Int. Cl.
*A61B 5/1459* (2006.01)
*A61F 13/02* (2006.01)
(Continued)

(52) U.S. Cl.
CPC .......... *A61B 5/6886* (2013.01); *A61B 5/0071* (2013.01); *A61B 5/0531* (2013.01);
(Continued)

(58) Field of Classification Search
CPC ................ A61B 5/6886; A61B 5/0071; A61B 5/0531; A61B 5/14539; A61B 5/14552;
(Continued)

(56) References Cited

U.S. PATENT DOCUMENTS

| | | |
|---|---|---|
| 3,896,802 A | 7/1975 | Williams |
| 4,334,530 A | 6/1982 | Hassell |
| 5,090,410 A | 2/1992 | Saper |

(Continued)

FOREIGN PATENT DOCUMENTS

| | | |
|---|---|---|
| CN | 105232229 A | 1/2016 |
| CN | 105395184 A | 3/2016 |

(Continued)

OTHER PUBLICATIONS

International Search Report and Written Opinion, re PCT Application No. PCT/EP2018/066569, dated Oct. 9, 2018.

(Continued)

*Primary Examiner* — Eric F Winakur
(74) *Attorney, Agent, or Firm* — Knobbe, Martens, Olson & Bear LLP

(57) ABSTRACT

Embodiments of apparatuses and methods for determining an emplacement of sensors in a wound dressing are disclosed. In some embodiments, a wound dressing includes a plurality of sensors configured to measure wound or patient characteristics. One or more processors are configured to receive wound or patient characteristics data as well as emplacement data. The received data can be used to determine an emplacement of the plurality of sensors, the wound dressing, or a wound. The sensors can include a set of (Continued)

nanosensors. The wound dressing can include pH sensitive ink which can be utilized for determining a placement of the wound dressing and determining a pH associated with the wound. The wound dressing can be used in a negative pressure wound therapy system.

20 Claims, 20 Drawing Sheets

(51) Int. Cl.
    *A61F 13/08*         (2006.01)
    *A61B 5/1455*       (2006.01)
    *A61B 5/053*        (2021.01)
    *A61B 5/00*         (2006.01)
    *A61B 5/0531*       (2021.01)
    *A61B 5/145*        (2006.01)
    *A61M 1/00*        (2006.01)

(52) U.S. Cl.
    CPC ........ *A61B 5/1459* (2013.01); *A61B 5/14539* (2013.01); *A61B 5/14552* (2013.01); *A61B 5/445* (2013.01); *A61B 5/6833* (2013.01); *A61B 5/6844* (2013.01); *A61F 13/0206* (2013.01); *A61F 13/08* (2013.01); *A61M 1/90* (2021.05)

(58) Field of Classification Search
    CPC ..... A61B 5/1459; A61B 5/445; A61B 5/6833; A61B 5/6844; A61F 13/08
    See application file for complete search history.

(56) References Cited

U.S. PATENT DOCUMENTS

| | | | |
|---|---|---|---|
| 5,107,862 A | 4/1992 | Fabian et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |

(56) References Cited

U.S. PATENT DOCUMENTS

| | | |
|---|---|---|
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berne, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0028717 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |

(56) References Cited

U.S. PATENT DOCUMENTS

| | | | |
|---|---|---|---|
| 2017/0146474 A1 | 5/2017 | Bedell et al. |
| 2017/0156594 A1 | 6/2017 | Stivoric |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0000817 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0078499 A1 | 3/2020 | Gadde et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0330258 A1 | 10/2020 | Hansen et al. |

FOREIGN PATENT DOCUMENTS

| | | |
|---|---|---|
| CN | 106102322 A | 11/2016 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3499510 A1 | 6/2019 |
| GB | 2316171 A | 2/1998 |
| GB | 2563602 A | 12/2018 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-20009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011113070 A1 | 9/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2014116816 A1 | 7/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016109744 A1 | 7/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018006584 A1 | 1/2018 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018162728 A2 | 9/2018 |
| WO | WO-2018185138 A1 | 10/2018 |
| WO | WO-2018189265 A1 | 10/2018 |
| WO | WO-2018209090 A1 | 11/2018 |
| WO | WO-2018210692 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A1 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |

(56) References Cited

FOREIGN PATENT DOCUMENTS

| WO | WO-2019238197 A1 | 12/2019 |
|---|---|---|
| WO | WO-2019238198 A1 | 12/2019 |

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.
Farooqui M.F., et al., "Low Cost Inkjet Printed Smart Bandage for Wireless Monitoring of Chronic Wounds," Scientific Reports, vol. 6, Jun. 29, 2016, 14 pages.
Geng Y., et al., "A Hybrid Low Power Biopatch for Body Surface Potential Measurement," IEEE Journal of Biomedical and Health Informatics, vol. 17, No. 3, May 1, 2013, pp. 591-599.
Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.
International Preliminary Report on Patentability for Application No. PCT/EP2018/066569, dated Jan. 2, 2020, 11 pages.
Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.
Little Miss Plasters, kidstravelclub.co.uk., retrieved from http://www.kidstravelclub.co.uk/little-miss-girls-childrens-plasters on Aug. 26, 2016, 2 pages.
Lu B., et al., "A Study of the Autofluorescence of Parylene Materials for µTAS Applications," Lab on Chip, vol. 10 (14), Jul. 2010, pp. 1826-1834.
McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.
Mostafalu P., et al., "Wireless Flexible Smart Bandage for Continuous Monitoring of Wound Oxygenation," IEEE Transactions on Biomedical Circuits and Systems, vol. 9 (5), Oct. 2015, pp. 670-677 (8 pages).
Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.
Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.
Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.
Wakita J., et al., "Variations in Optical Absorption and Fluorescence Spectra for Polyimide Thin Films Caused by Structural Isomerism," Journal of Photopolymer Science and Technology, Jan. 1, 2003, 1 page.
Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.
Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.
Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

POSITIONING OF SENSORS FOR SENSOR ENABLED WOUND MONITORING OR THERAPY

CROSS-REFERENCE TO RELATED APPLICATIONS

This application is a national stage application of International Patent Application No. PCT/EP2018/066569, filed Jun. 21, 2018, entitled "POSITIONING OF SENSORS FOR SENSOR ENABLED WOUND MONITORING OR THERAPY," which claims priority to U.S. Patent Application No. 62/524,413, filed on Jun. 23, 2017, entitled "POSITIONING OF SENSORS FOR SENSOR ENABLED NEGATIVE PRESSURE WOUND MONITORING AND THERAPY APPARATUS," each of which is hereby incorporated herein by reference in its entirety.

FIELD

Embodiments of the present disclosure relate to apparatuses, systems, and methods for the treatment of tissues via sensor-enabled monitoring in communication with various therapy regimes.

BACKGROUND

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

However, prior art dressings for use in negative pressure wound therapy or other wound therapy provide little visualization or information of the condition of the wound beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited and/or unsatisfactory methods or features of providing information of conditions of the wound.

SUMMARY

The present disclosure provides improved apparatuses and methods for determining an emplacement of sensors in a wound dressing. A wound monitoring and/or therapy system can include a wound dressing and a controller. The wound dressing can be configured to be positioned in contact with a wound. The wound dressing can include a plurality of sensors configured to measure a plurality of wound characteristics. The controller can include one or more processors. The controller can be configured to communicate with at least some of the plurality of sensors. The controller can be configured to receive emplacement data associated with a position or orientation of a point of reference. The controller can be configured to determine a position and/or orientation of the at least one point of reference relative to the wound based at least in part on the received emplacement data. The controller can be configured to determine a position and/or orientation in the wound of a first sensor of the plurality of sensors based at least in part on the determined position and/or orientation of the at least one point of reference. The controller can be configured to compare the position and/or orientation of the first sensor of the plurality of sensors with threshold emplacement data indicating correct position and/or orientation in the wound of the first sensor of the plurality of sensors. The controller can be configured to provide an indication that the first sensor of the plurality of sensors is correctly positioned in the wound, based at least on the comparison.

The system of the preceding paragraph may also include any combination of the following features described in this paragraph, among others described herein. The plurality of sensors can include at least one nanosensor, thermistor, conductivity sensor, Sp02 sensor, pH sensor, color sensor, optical sensor, impedance sensor, or electrode. The optical sensor can include at least one of a red, green, blue, and clear (RGBC) sensor or red, green blue, and white (RGBW) sensor. The first sensor can be a sensor other than an emplacement sensor configured to detect the emplacement data. The first sensor can be an emplacement sensor configured to detect the emplacement data. The system can include an emplacement sensor configured to detect the emplacement data. The emplacement sensor can include at least one of an external video camera or radio frequency (RF) sensor. The emplacement sensor can be embedded in the wound dressing. The point of reference can correspond to a position or orientation of an emplacement sensor configured to detect the emplacement data. The point of reference can correspond to a location that is remote from the wound dressing.

The system of any of the preceding paragraphs may also include any combination of the following features described in this paragraph, among others described herein. The controller can be configured to determine a position and/or orientation in the wound of a second sensor of the plurality of sensors based at least on the received emplacement data and a relationship between positions and/or orientations in the wound dressing and/or the wound of first and second sensors. The relationship can include at least known position and/or orientation can be configured to communicate and/or co-register with each other. The controller can be configured to provide the indication further based on co-registration data. At least one of the plurality of sensors can be configured with adjustable sensor settings. The adjustable sensor settings can be configured to be adjusted based at least in part on the received emplacement data. The wound dressing can be configured to communicate negative pressure to the wound.

A kit can include of any of the features described in this paragraph or in any of the preceding paragraphs, among others described herein. The kit can include a wound dressing and a negative pressure source configured to be fluidically connected to the wound dressing.

The present disclosure also provides a method of operating a wound monitoring and/or therapy system. The system can include a wound dressing that includes a plurality of sensors configured to measure a plurality of wound characteristics. The method can include receiving emplacement data associated with at least one point of reference, and determining a position and/or orientation of a first sensor of the plurality of sensors based at least in part on the received emplacement data. The method can further include comparing the position and/or orientation of the first sensor of the plurality of sensors with threshold emplacement data indicating correct position and/or orientation in the wound of the first sensor of the plurality of sensors. The method can further include providing an indication that the first sensor of the plurality of sensors is correctly positioned in the wound based at least in part on the comparison. The method can be performed by a controller of the wound monitoring and/or therapy system.

The method of the preceding paragraph may also include any combination of the following features or steps described in this paragraph, among others described herein. The plurality of sensors can include at least one nanosensor, thermistor, conductivity sensor, Sp02 sensor, pH sensor, color sensor, optical sensor, impedances sensor, emplacement sensor configured to detect the emplacement data, or electrode. The first sensor can include a sensor other than an emplacement sensor. The first sensor can be an emplacement sensor configured to detect the emplacement data. The point of reference can correspond to a position or orientation of an emplacement sensor configured to detect the emplacement data. The point of reference can correspond to a location that is remote from the wound dressing.

The method of any of the preceding paragraphs may also include any combination of the following features or steps described in this paragraph, among others described herein. The method can further include determining a position and/or orientation in the wound of a second sensor of the plurality of sensors based at least on the received emplacement data and a relationship between positions and/or orientations in the wound dressing and/or the wound of first and second sensors. The relationship can include at least known position and/or orientation offset between first and second sensors. At least some of the plurality of sensors can be configured to communicate and/or co-register with each other. The method can further include providing the indication further based on co-registration data. At least one of the plurality of sensors can be configured with adjustable sensor settings. The method can further include adjusting the adjustable sensor settings based at least in part on the received emplacement data. The method can further include communicating negative pressure to the wound.

The present disclosure also provides a wound monitoring and/or therapy system. The system can include a wound dressing and a position sensing device. The wound dressing can be configured to be positioned in contact with a wound, the wound dressing comprising a plurality of sensors configured to measure a plurality of wound characteristics and at least one alignment feature is associated with a position and/or orientation of the wound dressing. The positioning sensing device can include a sensor and a controller including one or more processors. The controller can be configured to communicate with the sensor. The controller can also be configured to determine a position and/or orientation of the at least one alignment feature based at least in part on data received from the sensor. The controller can also be configured to determine a position and/or orientation in the wound of at least one sensor from the plurality of sensors of the wound dressing based at least in part on the determined position and/or orientation of the at least one alignment feature. The controller can also be configured to provide an indication of a status of the position of the at least one sensor from the plurality of sensors relative to the wound.

The system of any of the preceding paragraphs may also include any combination of the following features described in this paragraph, among others described herein. The at least one alignment feature can include a marking. The marking can be positioned on the wound dressing. The marking can be positioned on or near a periphery of the wound. The marking can include pH-sensitive ink. The pH-sensitive ink can include at least one of pH-sensitive ink, dye, or pigment and can be configured to change color in response to pH alterations in a wound environment. The controller of the positioning sensing device can be further configured to measure a change in color of the pH-sensitive ink. The sensor of the positioning sensing device can include at least one of an optical pH sensor or a scanner. The data received from the sensor of the positioning sensing device can include at least one of an angle of the at least one alignment feature relative to the positioning sensing device, an angle of the at least one alignment feature relative to a trajectory of a scan beam of the positioning sensing device, a distance between the at least one alignment feature and the positioning sensing device, a size corresponding to the at least one alignment feature, a skew corresponding to the at least one alignment feature, or an angular amount of parallax corresponding to the at least one alignment feature.

The system of any of the preceding paragraphs may also include any combination of the following features described in this paragraph, among others described herein. The at least one alignment features can include at least one of a barcode, a number, a letter, an alphanumeric code, a standard shape, an irregular shape, or a logo. The position and/or orientation of the at least one alignment feature relative to the wound includes at least one of a depth of the at least one sensor of the plurality of sensors in the wound, a distance of the at least one sensor from a portion of the wound, an orientation of the at least one sensor, or a position of the at least one sensor on the wound. The at least one alignment feature can be associated with a value and the value can identify a baseline position of the at least one alignment feature relative to a flat dressing. The at least one alignment feature can include two alignment features. The status can include an indication that the at least one sensor is correctly positioned in the wound. The status can include an indication that the at least one sensor is not correctly positioned in the wound.

The present disclosure also provides a method of operating a wound monitoring and/or therapy system. The system can include a wound dressing that includes a plurality of sensors configured to measure a plurality of wound characteristics. The method can include receiving, from a positioning sensing device, emplacement data associated with a position or orientation of a point of reference. The wound dressing can be in contact with a wound of a patient and comprises a plurality of sensors configured to measure a plurality of wound characteristics. The method can include determining, based at least in part on the received emplacement data, a position and/or orientation of the at least one point of reference relative to the wound. The method can include determining, based at least in part on the determined position and/or orientation of the at least one point of reference, a position and/or orientation in the wound of a first sensor from the plurality of sensors of the wound dressing. The method can include indicating a status of the position and/or orientation in the wound of the at least one sensor.

The method of any of the preceding paragraphs may also include any combination of the following features or steps described in this paragraph, among others described herein. The plurality of sensors can include at least one nanosensor, thermistor, conductivity sensor, Sp02 sensor, pH sensor, color sensor, optical sensor, impedance sensor, or electrode. The optical sensor can include at least one of a red, green, blue, and clear (RGBC) sensor or red, green blue, and white (RGBW) sensor. The first sensor can include a sensor other than an emplacement sensor configured to detect the emplacement data. The first sensor is an emplacement sensor configured to detect the emplacement data. The emplacement sensor can include at least one of an external video camera or radio frequency (RF) sensor. The emplacement sensor can be embedded in the wound dressing. The point of reference can correspond to a position or orientation of an emplacement sensor configured to detect the emplacement data. The point of reference can correspond to a location that is remote from the wound dressing.

The method of any of the preceding paragraphs may also include any combination of the following features or steps described in this paragraph, among others described herein. The method can include determining a position and/or orientation in the wound of a second sensor of the plurality of sensors based at least on a relationship between positions and/or orientations in the wound dressing and/or the wound of first and second sensors. The relationship can include at least known position and/or orientation offset between first and second sensors. At least some of the plurality of sensors can be configured to communicate and/or co-register with each other. The method can include providing the indication further based on co-registration data. At least one of the plurality of sensors can be configured with adjustable sensor settings. The method can include adjusting the adjustable sensor settings based at least in part on the received emplacement data. The wound dressing can be configured to communicate negative pressure to the wound. A sensor of the positioning sensing device can include at least one of an optical pH sensor or a scanner. At least one alignment feature can be associated with a position and/or orientation of the wound dressing.

The method of any of the preceding paragraphs may also include any combination of the following features or steps described in this paragraph, among others described herein. The emplacement data received from the positioning sensing device can include at least one of an angle of the at least one alignment feature relative to the positioning sensing device, an angle of the at least one alignment feature relative to a trajectory of a scan beam of the positioning sensing device, a distance between the at least one alignment feature and the positioning sensing device, a size corresponding to the at least one alignment feature, a skew corresponding to the at least one alignment feature, or an angular amount of parallax corresponding to the at least one alignment feature. The at least one alignment feature can include at least one of a barcode, a number, a letter, an alphanumeric code, a standard shape, an irregular shape, or a logo. The position and/or orientation of the at least one alignment feature relative to the wound can include at least one of a depth of the at least one sensor in the wound, a distance of the at least one sensor from a portion of the wound, an orientation of the at least one sensor, or a position of the at least one sensor on the wound. The at least one alignment feature can be associated with a value and the value can identify a baseline position of the alignment feature relative to a flat dressing.

The method of any of the preceding paragraphs may also include any combination of the following features or steps described in this paragraph, among others described herein. The alignment feature can include pH-sensitive ink. The pH-sensitive ink can be configured to change color in response to pH alterations in a wound environment. The method can include measuring a change in color of the pH-sensitive ink. The at least one alignment feature can include two markings. Indicating the status can further include indicating that the at least one sensor is correctly positioned in the wound. Indicating the status can further include indicating that the at least one sensor is not correctly positioned in the wound.

In some embodiments, a wound monitoring system includes a wound dressing and a controller. The wound dressing is configured to be positioned in contact with a wound and the wound dressing includes a plurality of sensors. The plurality of sensors is configured to measure a plurality of wound characteristics. The plurality of sensors includes at least one emplacement sensor configured to determine position and/or orientation in the wound of a first sensor of the plurality of sensors. The controller includes one or more processors. The controller is configured to be communicatively coupled to at least some of the plurality of sensors. The controller is further configured to receive emplacement data from the at least one emplacement sensor, wherein the emplacement data indicates the position and/or orientation in the wound of the first sensor of the plurality of sensors. The controller is further configured to compare the received emplacement data with threshold emplacement data indicating correct position and/or orientation in the wound of the first sensor of the plurality of sensors. The controller is further configured to, based at least on the comparison, provide an indication that the first sensor of the plurality of sensors is correctly positioned in the wound.

The system of any of the preceding paragraphs may also include any combination of the following features described in the paragraph, among other features described herein. In some embodiments, the plurality of sensors includes at least one nanosensor, thermistor, conductivity sensor, Sp02 sensor, pH sensor, color sensor, optical sensor, or electrode. In some embodiments, the first sensor is a sensor other than the emplacement sensor. In some embodiments, the first sensor is the emplacement sensor.

The system of any of the preceding paragraphs may also include any combination of the following features described in the paragraph, among other features described herein. In some embodiments, the controller is further configured to determine a position and/or orientation in the wound of a second sensor of the plurality of sensors based at least on the received emplacement data and a relationship between positions and/or orientations in the wound dressing and/or the wound of first and second sensors. In some embodiments, thee relationship includes at least known position and/or orientation offset between first and second sensors.

The system of any of the preceding paragraphs may also include any combination of the following features described in the paragraph, among other features described herein. In some embodiments, at least some of the plurality of sensors are configured to communicate and/or co-register with each other, and wherein the controller is configured to provide the indication further based on co-registration data. In some embodiments, at least one of the plurality of sensors includes adjustable sensor settings, and wherein the adjustable sensor settings are configured to be adjusted based at least in part on the received emplacement data. In some embodiments, the wound dressing is configured to communicate negative pressure to the wound.

In some embodiments, a kit including the wound dressing and of the features of any of the preceding paragraphs and a negative pressure source configured to be fluidically connected to the wound dressing is provided.

In some embodiments, a method of operating a wound monitoring system includes a wound dressing including a plurality of sensors configured to measure a plurality of wound characteristics. The method includes receiving emplacement data from at least one emplacement sensor positioned in the wound dressing. The emplacement data indicates position and/or orientation in the wound of a first sensor from the plurality of sensors. The method further includes comparing the received emplacement data with threshold emplacement data indicating correct position and/ or orientation in the wound of the first sensor of the plurality of sensors. The method further includes, based at least on the comparison, providing an indication that the first sensor of the plurality of sensors is correctly positioned in the wound. In some embodiments, a controller of the wound monitoring system performs the method.

The method of any of the preceding paragraphs may also include any combination of the following steps or features described in the paragraph, among other steps or features described herein. In some embodiments, the plurality of sensors includes at least one nanosensor, thermistor, conductivity sensor, Sp02 sensor, pH sensor, color sensor, optical sensor, or electrode. In some embodiments, the first sensor is a sensor other than the emplacement sensor. In some embodiments, the first sensor is the emplacement sensor.

The method of any of the preceding paragraphs may also include any combination of the following steps or features described in the paragraph, among other steps or features described herein. In some embodiments, the method can further include determining a position and/or orientation in the wound of a second sensor of the plurality of sensors based at least on the received emplacement data and a relationship between positions and/or orientations in the wound dressing and/or the wound of first and second sensors. In some embodiments, the relationship includes at least known position and/or orientation offset between first and second sensors. In some embodiments, at least some of the plurality of sensors are configured to communicate and/or co-register with each other, the method further includes providing the indication further based on co-registration data.

The method of any of the preceding paragraphs may also include any combination of the following steps or features described in the paragraph, among other steps or features described herein. In some embodiments, at least one of the plurality of sensors includes adjustable sensor settings and the method further includes adjusting the adjustable sensor settings based at least in part on the received emplacement data. In some embodiments, the method further includes communicating negative pressure to the wound.

In some embodiments, a wound monitoring system includes a wound dressing and a positioning sensing device. The wound dressing is configured to be positioned in contact with a wound. The wound dressing includes a plurality of sensors configured to measure a plurality of wound characteristics. The wound dressing further includes at least one marking positioned on the wound dressing. The at least one marking includes pH-sensitive ink. The positioning sensing device includes a sensor and a controller. The controller includes one or more processors. The controller is configured to be communicatively coupled to the sensor and further configured to based at least in part on data received from the sensor, determine a position and/or orientation of the at least one marking relative to the wound. The controller is further configured to, based at least in part on the determined position and/or orientation of the at least one marking, determine a position and/or orientation in the wound of at least one sensor from the plurality of sensors of the wound dressing. The controller is further configured to provide an indication of a status of the position of the at least one sensor relative to the wound.

The system of any of the preceding paragraphs may also include any combination of the following features described in the paragraph, among other features described herein. In some embodiments, the sensor of the positioning sensing device includes at least one of an optical pH sensor or a scanner. In some embodiments, the data received from the sensor includes at least one of an angle of the at least one marking relative to the positioning sensing device, an angle of the at least one marking relative to a trajectory of a scan beam of the positioning sensing device, a distance between the at least one marking and the positioning sensing device, a size corresponding to the at least one marking, a skew corresponding to the at least one marking, or an angular amount of parallax corresponding to the at least one marking.

The system of any of the preceding paragraphs may also include any combination of the following features described in the paragraph, among other features described herein. In some embodiments, at least one marking includes at least one of a barcode, a number, a letter, an alphanumeric code, a standard shape, an irregular shape, or a logo. In some embodiments, the position and/or orientation of the at least one marking relative to the wound includes at least one of a depth of the at least one sensor in the wound, a distance of the at least one sensor from a portion of the wound, an orientation of the at least one sensor, or a position of the at least one sensor on the wound. In some embodiments, the at least one marking is associated with a value and the value can identify a baseline position of the marking relative to a flat dressing.

The system of any of the preceding paragraphs may also include any combination of the following features described in the paragraph, among other features described herein. In some embodiments, the pH-sensitive ink includes at least one of pH-sensitive ink, dye, or pigment and is configured to change color in response to pH alterations in a wound environment. In some embodiments, the controller of the positioning sensing device is further configured to measure a change in color of the pH-sensitive ink. In some embodiments, the at least one marking includes two markings. In some embodiments, the status includes an indication that the at least one sensor is correctly positioned in the wound. In some embodiments, the status includes an indication that the at least one sensor is not correctly positioned in the wound.

In some embodiments, a method of operating a wound monitoring system includes a wound dressing. The wound dressing includes a plurality of sensors configured to measure a plurality of wound characteristics and the wound dressing further includes a marking positioned on the wound dressing. The method includes receiving, from a positioning sensing device, emplacement data corresponding to at least one marking that is positioned on a wound dressing. The at least one marking includes pH-sensitive ink. The wound dressing is in contact with a wound of a patient and includes a plurality of sensors configured to measure a plurality of wound characteristics. The method further includes determining, based at least in part on the received emplacement data, a position and/or orientation of the at least one marking relative to the wound. The method further includes determining, based at least in part on the determined position and/or orientation of the at least one marking, a position and/or orientation in the wound of at least one sensor from the plurality of sensors of the wound dressing. The method further includes indicating a status of the position and/or orientation in the wound of the at least one sensor.

The method of any of the preceding paragraphs may also include any combination of the following steps or features described in the paragraph, among other steps or features described herein. In some embodiments, the sensor of the positioning sensing device includes at least one of an optical pH sensor or a scanner. In some embodiments, the data received from the sensor includes at least one of an angle of the at least one marking relative to the positioning sensing device, an angle of the at least one marking relative to a trajectory of a scan beam of the positioning sensing device, a distance between the at least one marking and the positioning sensing device, a size corresponding to the at least one marking, a skew corresponding to the at least one marking, or an angular amount of parallax corresponding to the at least one marking.

The method of any of the preceding paragraphs may also include any combination of the following steps or features described in the paragraph, among other steps or features described herein. In some embodiments, the at least one marking includes at least one of a barcode, a number, a letter, an alphanumeric code, a standard shape, an irregular shape, or a logo. In some embodiments, the position and/or orientation of the at least one marking relative to the wound includes at least one of a depth of the at least one sensor in the wound, a distance of the at least one sensor from a portion of the wound, an orientation of the at least one sensor, or a position of the at least one sensor on the wound. In some embodiments, the at least one marking is associated with a value and the value can identify a baseline position of the marking relative to a flat dressing.

The method of any of the preceding paragraphs may also include any combination of the following steps or features described in the paragraph, among other steps or features described herein. In some embodiments, the pH-sensitive ink is configured to change color in response to pH alterations in a wound environment. In some embodiments, the method further includes measuring a change in color of the pH-sensitive ink. In some embodiments, the at least one marking includes two markings. In some embodiments, the method further includes indicating that the at least one sensor is correctly positioned in the wound. In some embodiments, the method further includes indicating that the at least one sensor is not correctly positioned in the wound.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

DETAILED DESCRIPTION

Figure 1A:
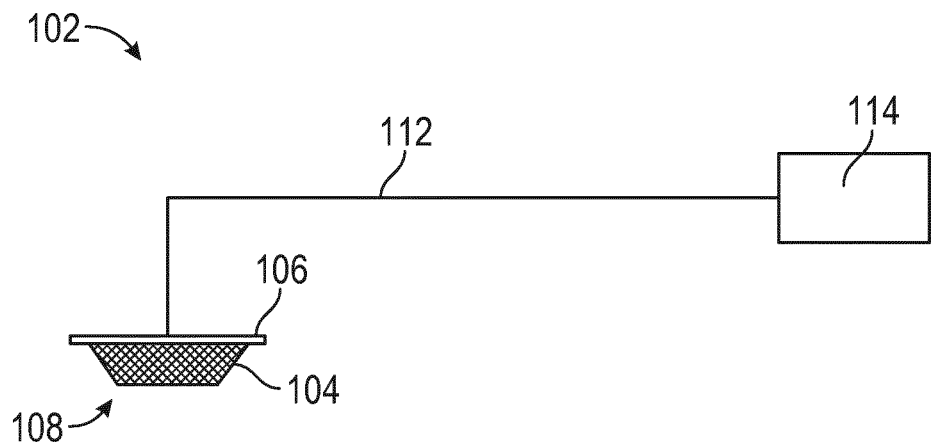
FIG. 1A illustrates a negative pressure wound treatment system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing.

A non-negative pressure wound dressing suitable for providing protection at a wound site may comprise:
an absorbent layer for absorbing wound exudate and
an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapour permeability of 500 g/m2/24 hours or more.

The translucent film may be a bacterial barrier.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.
The apertures may have an area from 0.005 to 0.32 mm2.
The support layer may have a tensile strength from 0.05 to 0.06 Nm.
The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing assembly, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

NPWT System Overview

FIG. 1A illustrates an embodiment of a negative or reduced pressure wound treatment (or TNP) system 102 comprising a wound filler 108 placed inside a wound cavity 104, the wound cavity sealed by a wound cover 106. The wound filler 108 in combination with the wound cover 106 can be referred to as wound dressing. A single or multi lumen tube or conduit 112 is connected the wound cover 106 with a pump assembly 114 configured to supply reduced pressure. The wound cover 106 can be in fluidic communication with the wound cavity 104. In any of the system embodiments disclosed herein, as in the embodiment illustrated in FIG. 1A, the pump assembly can be a canisterless pump assembly (meaning that exudate is collected in the wound dressing or is transferred via tube 112 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 108 can be any suitable type, such as hydrophilic or hydrophobic foam, gauze, inflatable bag, and so on. The wound filler 108 can be conformable to the wound cavity 104 such that it substantially fills the cavity. The wound cover 106 can provide a substantially fluid impermeable seal over the wound cavity 104. The wound cover 106 can have a top side and a bottom side, and the bottom side adhesively (or in any other suitable manner) seals with wound cavity 104. The conduit 112 or lumen or any other conduit or lumen disclosed herein can be formed from polyurethane, PVC, nylon, polyethylene, silicone, or any other suitable material.

Some embodiments of the wound cover 106 can have a port (not shown) configured to receive an end of the conduit 112. For example, the port can be Renays Soft Port available from Smith & Nephew. In other embodiments, the conduit 112 can otherwise pass through or under the wound cover 106 to supply reduced pressure to the wound cavity 104 so as to maintain a desired level of reduced pressure in the wound cavity. The conduit 112 can be any suitable article configured to provide at least a substantially sealed fluid flow pathway between the pump assembly 114 and the wound cover 106, so as to supply the reduced pressure provided by the pump assembly 114 to wound cavity 104.

The wound cover 106 and the wound filler 108 can be provided as a single article or an integrated single unit. In some embodiments, no wound filler is provided and the wound cover by itself may be considered the wound dressing. The wound dressing may then be connected, via the conduit 112, to a source of negative pressure, such as the pump assembly 114. The pump assembly 114 can be miniaturized and portable, although larger conventional pumps such can also be used.

The wound cover 106 can be located over a wound site to be treated. The wound cover 106 can form a substantially sealed cavity or enclosure over the wound site. In some embodiments, the wound cover 106 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 114 and tubing 112 so that the tubing 112 can be quickly and easily removed from the pump assembly 114 can facilitate or improve the process of dressing or pump changes, if necessary. Any of the pump embodiments disclosed herein can be configured to have any suitable connection between the tubing and the pump.

The pump assembly 114 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 114.

In operation, the wound filler 108 is inserted into the wound cavity 104 and wound cover 106 is placed so as to seal the wound cavity 104. The pump assembly 114 provides a source of a negative pressure to the wound cover 106, which is transmitted to the wound cavity 104 via the wound filler 108. Fluid (such as, wound exudate) is drawn through the conduit 112, and can be stored in a canister. In some embodiments, fluid is absorbed by the wound filler 108 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Wound Dressing Overview

Figure 1B:
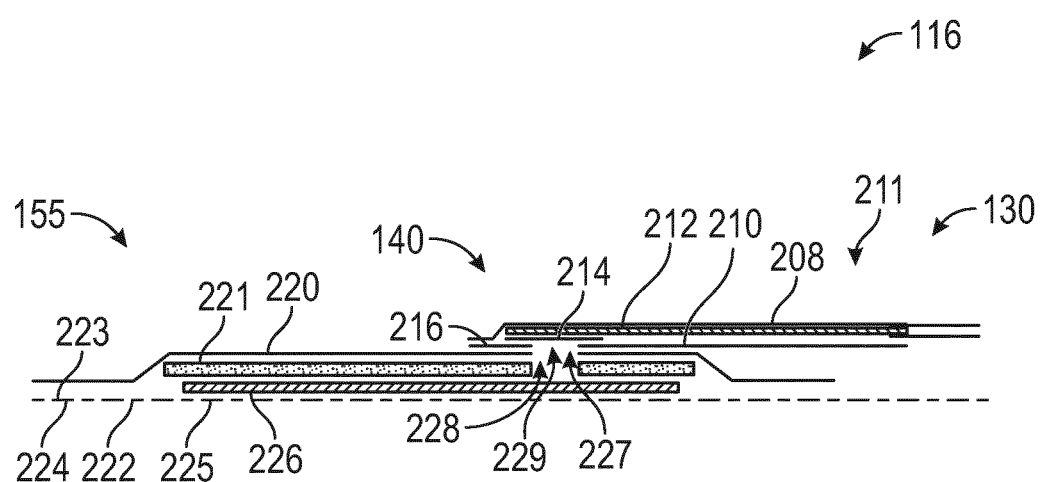
FIG. 1B illustrates a wound dressing according to some embodiments.

FIG. 1B illustrates a cross-section through a wound dressing 155 according to some embodiments. FIG. 1B also illustrates a fluidic connector 116 according to some embodiments. The wound dressing 155 can be similar to the wound dressing described in International Patent Publication WO2013175306 A2, which is incorporated by reference in its entirety. Alternatively, the wound dressing 155 can be any wound dressing embodiment disclosed herein or any combination of features of any number of wound dressing embodiments disclosed herein, can be located over a wound site to be treated. The wound dressing 155 may be placed as to form a sealed cavity over the wound, such as the wound cavity 104. In some embodiments, the wound dressing 155 includes a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some embodiments, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 155 while also creating an air tight seal around the absorbent pad in order to maintain negative pressure at the wound. In some embodiments, the wound contact layer is configured to allow unidirectional or substantially one-way or unidirectional flow of fluid through the wound contact layer when negative pressure is applied to the wound. For example, the wound contact layer can permit fluid to flow away from the wound through the wound contact layer, but not allow fluid to flow back toward the wound. In certain case, the perforations in the wound contact layer are configured to permit such one-way or unidirectional flow of fluid through the wound contact layer.

Some embodiments of the wound contact layer 222 may also act as a carrier for an optional lower and upper adhesive layer (not shown). For example, a lower pressure sensitive adhesive may be provided on the lower surface 224 of the wound dressing 155 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 155 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. An additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material can be provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 155 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™ 11C-450. In some embodiments, the absorbent layer 221 may comprise a composite comprising superabsorbent powder, fibrous material such as cellulose, and bonding fibers. In a some embodiments, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 155. In some embodiments, the fluidic connector 116 is attached or sealed to the top of the backing layer 220 over the orifice 227 made into the dressing 155, and communicates negative pressure through the orifice 227. A length of tubing may be coupled at a first end to the fluidic connector 116 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 116 may be adhered and sealed to the backing layer 220 using an adhesive such as an acrylic, cyanoacrylate, epoxy, UV curable or hot melt adhesive. The fluidic connector 116 may be formed from a soft polymer, for example a polyethylene, a polyvinyl chloride, a silicone or polyurethane having a hardness of 30 to 90 on the Shore A scale. In some embodiments, the fluidic connector 116 may be made from a soft or conformable material.

In some embodiments, the absorbent layer 221 includes at least one through hole 228 located so as to underlie the fluidic connector 116. The through hole 228 may in some embodiments be the same size as the opening 227 in the backing layer, or may be bigger or smaller. As illustrated in FIG. 1B a single through hole can be used to produce an opening underlying the fluidic connector 116. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 1B. This allows the negative pressure applied to the fluidic connector 116 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is can be gas impermeable, but moisture vapor permeable, and can extend across the width of the wound dressing 155. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can include two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 1B, the absorbent layer 221 may define a smaller perimeter than that of the backing layer 220, such that a boundary or border region is defined between the edge of the absorbent layer 221 and the edge of the backing layer 220.

As shown in FIG. 1B, one embodiment of the wound dressing 155 comprises an aperture 228 in the absorbent layer 221 situated underneath the fluidic connector 116. In use, for example when negative pressure is applied to the dressing 155, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

For example, in embodiments with a single fluidic connector 116 and through hole, it may be preferable for the fluidic connector 116 and through hole to be located in an off-center position. Such a location may permit the dressing 155 to be positioned onto a patient such that the fluidic connector 116 is raised in relation to the remainder of the dressing 155. So positioned, the fluidic connector 116 and the filter 214 may be less likely to come into contact with wound fluids that could prematurely occlude the filter 214 so as to impair the transmission of negative pressure to the wound site.

Turning now to the fluidic connector 116, some embodiments include a sealing surface 216, a bridge 211 with a proximal end (closer to the negative pressure source) and a distal end 140, and a filter 214. The sealing surface 216 can form the applicator that is sealed to the top surface of the wound dressing. In some embodiments a bottom layer of the fluidic connector 116 may comprise the sealing surface 216. The fluidic connector 116 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 116 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 155 similar to the suction adapter as described in U.S. Pat. No. 8,801,685, which is incorporated by reference herein in its entirety.

In some embodiment, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between −40 to −150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some embodiments, the filter element 214 is impermeable to liquids, but permeable to gases, and is provided to act as a liquid barrier and to ensure that no liquids are able to escape from the wound dressing 155. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 116, or may be adhered to one or both of the top of the cover layer and bottom of the suction adapter 160 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic copolymer membrane formed on the support layer. In some embodiments, the wound dressing 155 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 155 may comprise spacer elements 215 in conjunction with the fluidic connector 116 and the filter 214. With the addition of such spacer elements 215 the fluidic connector 116 and filter 214 may be supported out of direct contact with the absorbent layer 220 or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 1C:
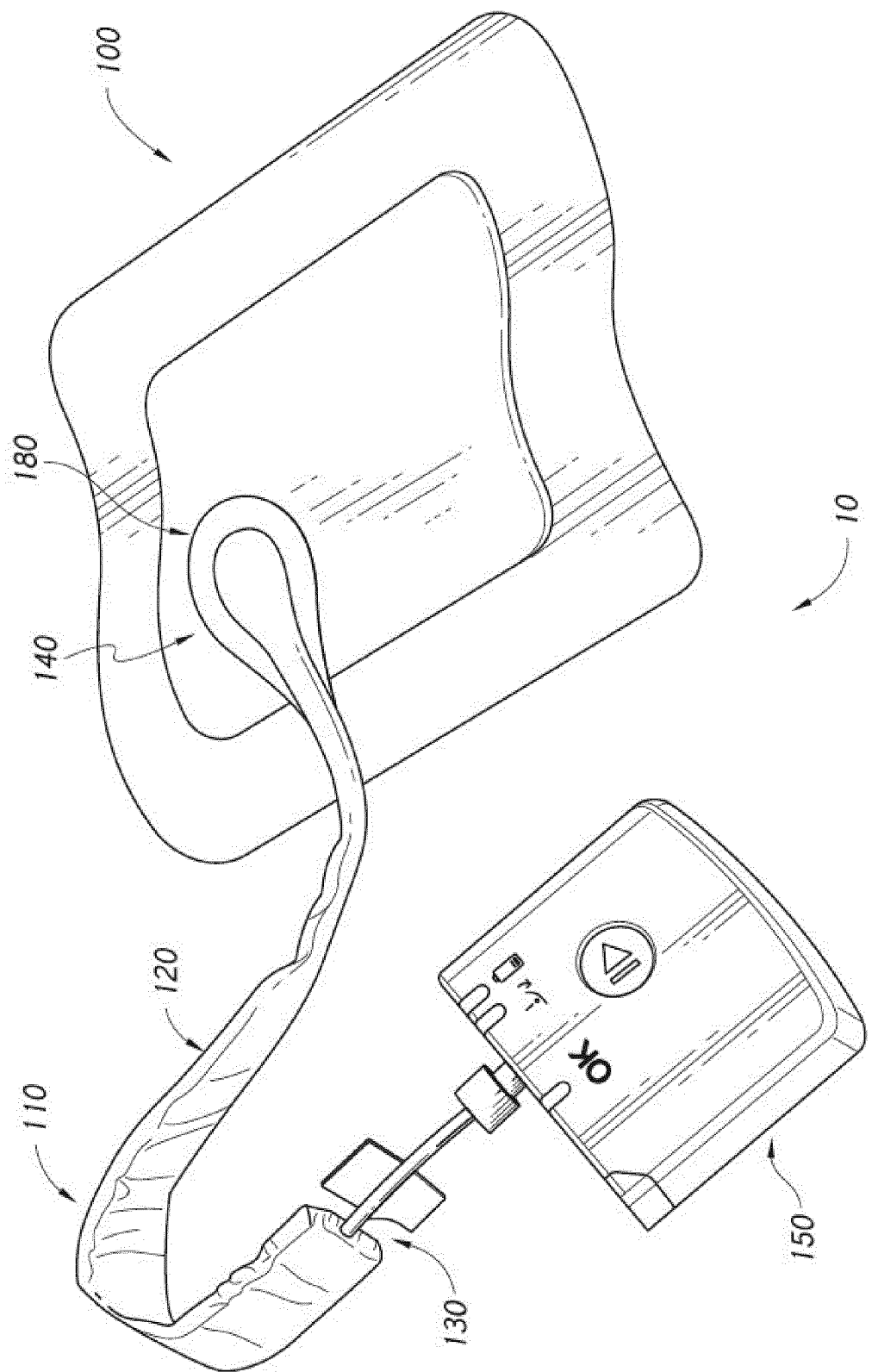
FIG. 1C illustrates a negative pressure wound treatment system employing a flexible fluidic connector and a wound dressing capable of absorbing and storing wound exudate according to some embodiments.
Figure 1D:
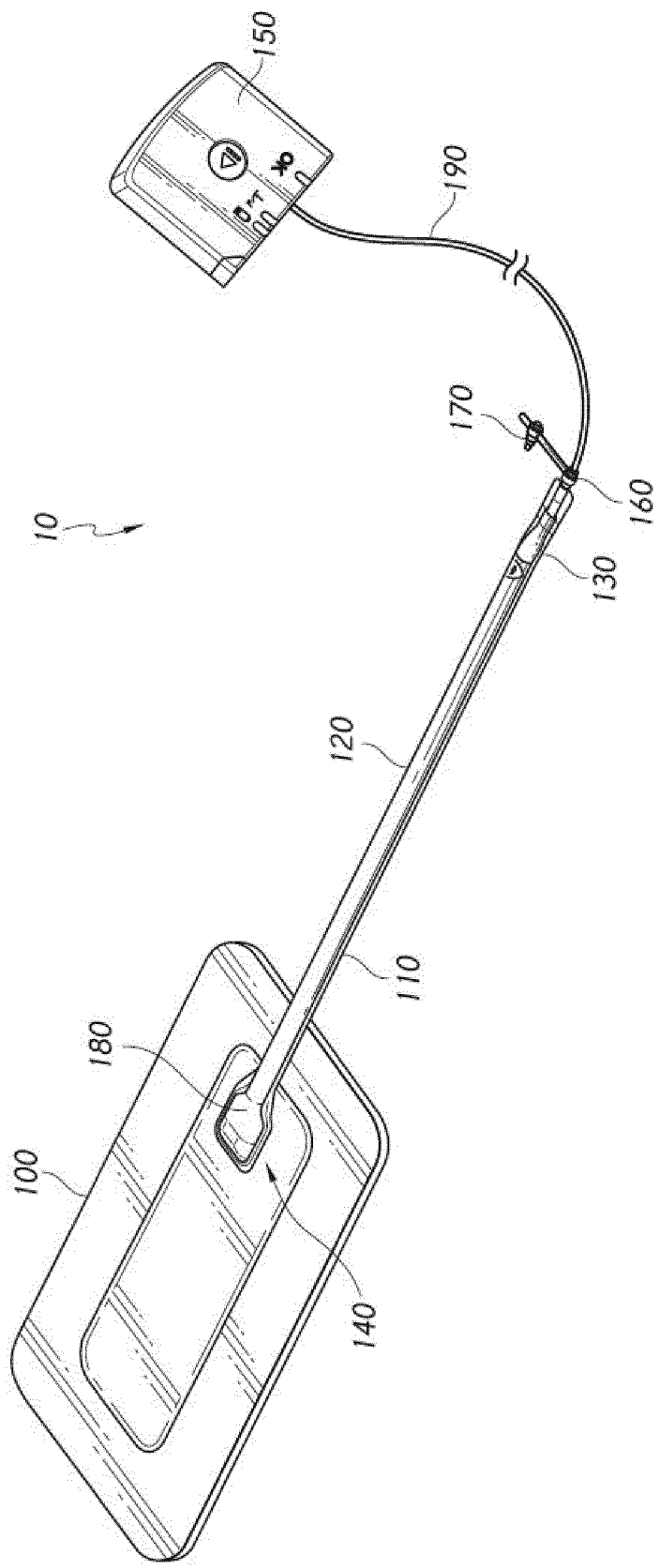
FIG. 1D illustrates a negative pressure wound treatment system employing a flexible fluidic connector and a wound dressing capable of absorbing and storing wound exudate according to some embodiments.

FIGS. 1C-1D illustrate embodiments of a negative pressure wound treatment system 10 employing a wound dressing 100 in conjunction with a fluidic connector 110. Here, the fluidic connector 110 may comprise an elongate conduit, for example, a bridge 120 having a proximal end 130 and a distal end 140, and an applicator 180 at the distal end 140 of the bridge 120. An optional coupling 160 can be disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 1E:
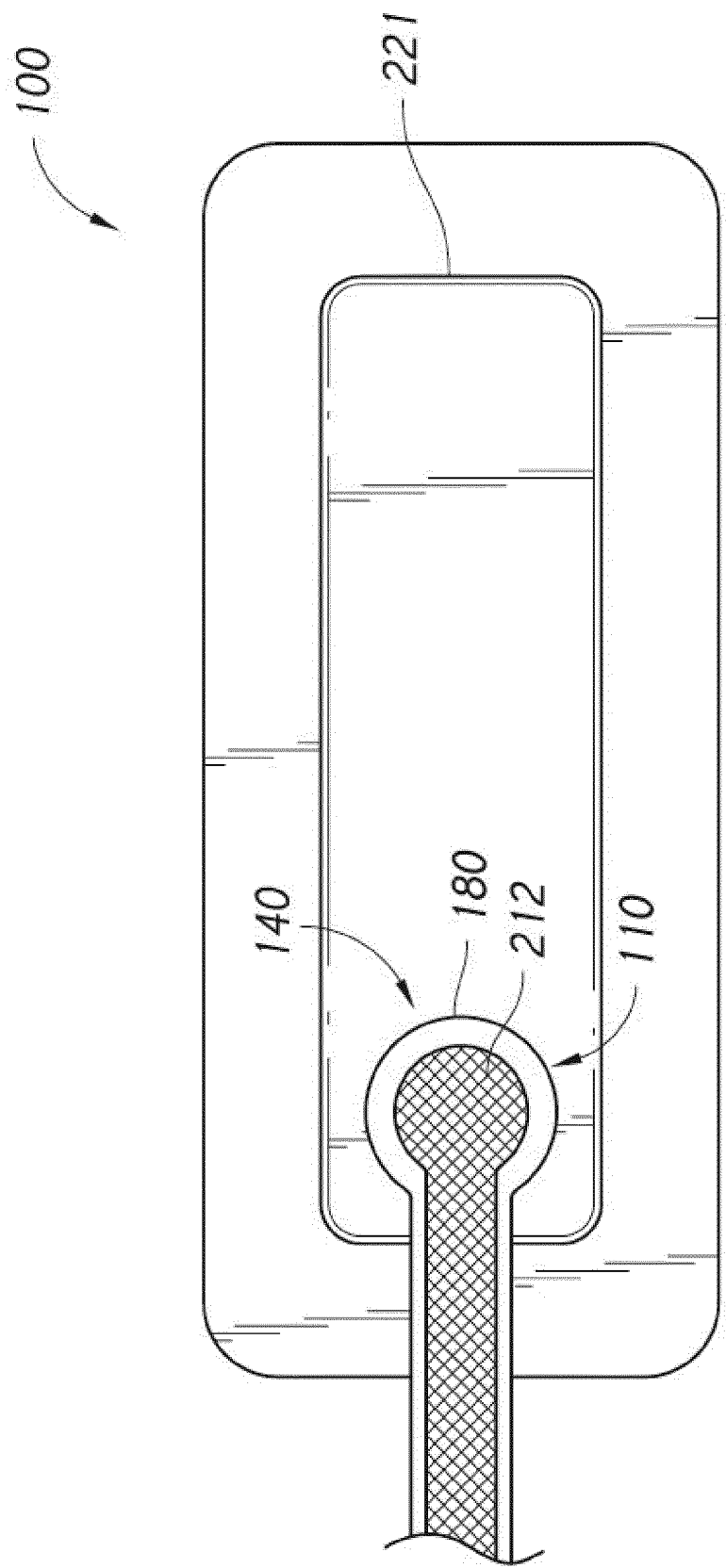
FIG. 1E illustrates a negative pressure wound treatment system employing a flexible fluidic connector and a wound dressing capable of absorbing and storing wound exudate according to some embodiments.

As shown in FIG. 1E, the fluidic connector 110 comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In an embodiment, the head 140 may measure 30 mm along its widest edge. The head 140 forms at least in part the applicator 180, described above, that is configured to seal against a top surface of the wound dressing.

Figure 1F:
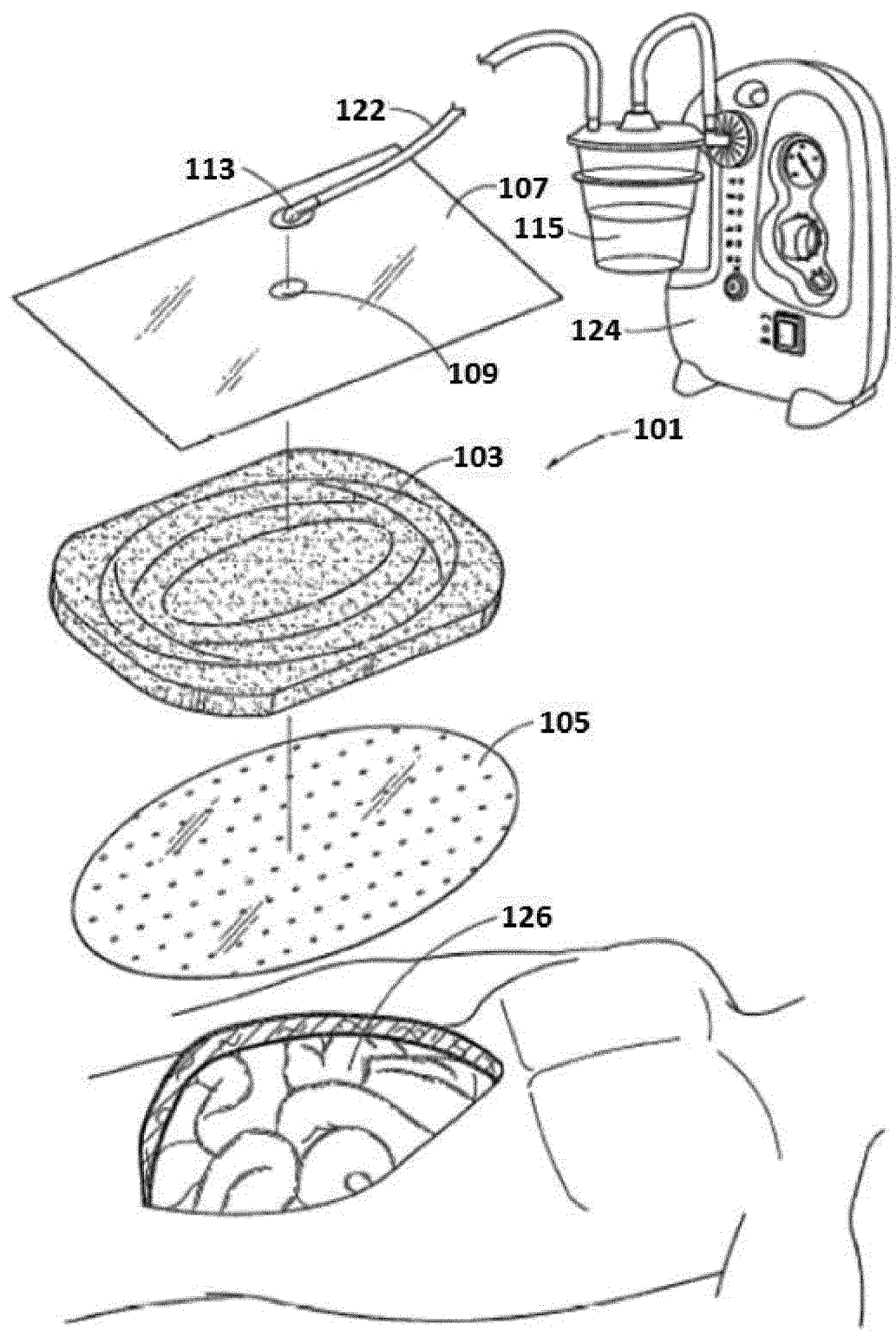
FIG. 1F illustrates of a negative pressure wound therapy system according to some embodiments.

Turning to FIG. 1F, treatment of other wound types, such as larger abdominal wounds, with negative pressure in certain embodiments uses a negative pressure treatment system 101 as illustrated schematically here. In this embodiment, a wound 126, illustrated here as an abdominal wound, may benefit from treatment with negative pressure. Such abdominal wounds may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound. The application of reduced or negative pressure to a wound has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound 106 can be beneficial to a patient.

Accordingly, certain embodiments provide for a wound contact layer 105 to be placed over the wound 126. The wound contact layer can also be referred to as an organ protection layer and/or a tissue protection layer. Preferably, the wound contact layer 105 can be a thin, flexible material which will not adhere to the wound or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound 126 or the transmittal of negative pressure to the wound 126. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound 126. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound 126. The drape 107 can be at least partially liquid impermeable, such that at least a partial negative pressure may be maintained at the wound. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 122. The conduit 122 may be connected to a port 113 situated over an aperture 109 in the drape 107, or else the conduit 122 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 124 and the conduit 122 so as to permit wound exudate and other fluids removed from the wound to be stored without entering the source of negative pressure. Certain types of negative pressure sources—for example, peristaltic pumps—may also permit a container 115 to be placed after the pump 124. Some embodiments may also use a filter to prevent fluids, aerosols, and other microbial contaminants from leaving the container 115 and/or entering the source of negative pressure 124. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 1G:
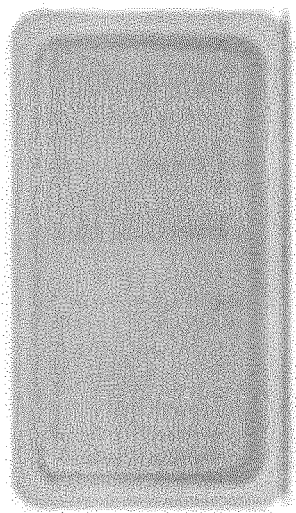
FIG. 1G illustrates a wound treatment system employing a wound dressing capable of absorbing and storing wound exudate to be used without negative pressure according to some embodiments.
Figure 1G:
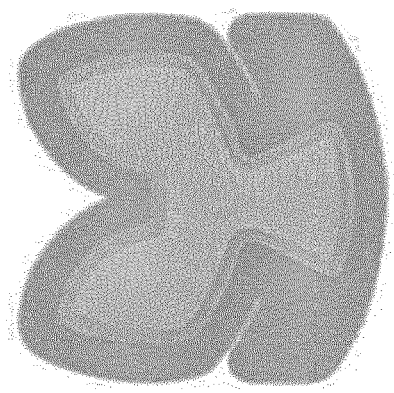
Figure 1G:
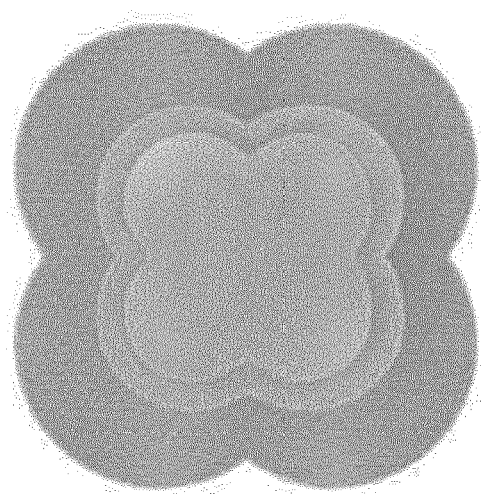
Figure 1G:
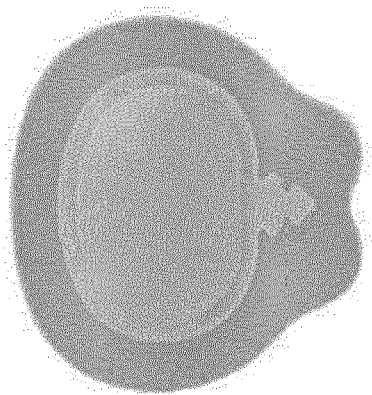

FIG. 1G illustrates various embodiments of a wound dressing that can be used for healing a wound without negative pressure. As shown in the dressings of FIG. 1G, the wound dressings can have multiple layers similar to the dressings described with reference to FIGS. 1C-1F except the dressings of FIG. 1G do not include a port or fluidic connector. The wound dressings of FIG. 1G can include a cover layer and wound contact layer as described herein. The wound dressing can include various layers positioned between the wound contact layer and cover layer. For example, the dressing can include one or more absorbent layers and/or one or more transmission layers as described herein with reference to FIGS. 1C-1F. Additionally, some embodiments related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to embodiments of wound dressings, the wound dressing components and principles, and the materials used for the wound dressings.

Wound Dressing with Sensors

A wound dressing that incorporates a number of sensors can be utilized in order to monitor characteristics of a wound as it heals. Collecting data from the wounds that heal well, and from those that do not, can provide useful insights towards identifying measurands to indicate whether a wound is on a healing trajectory.

Figure 2:
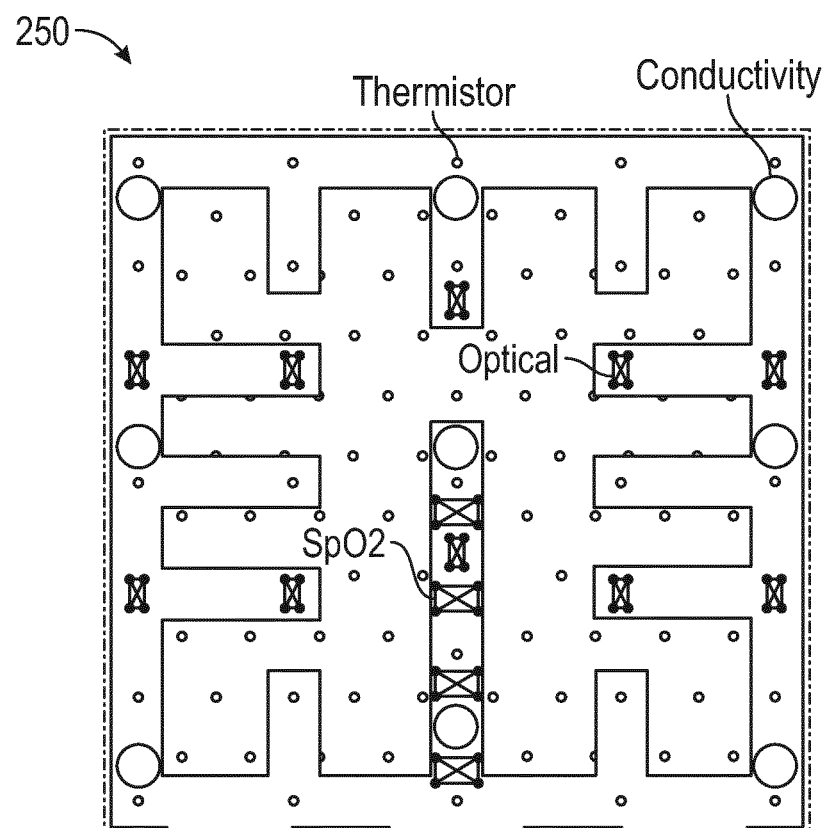
FIG. 2 illustrates a sensor array illustrating the sensor placement incorporated into a wound dressing according to some embodiments.
Figure 3A:
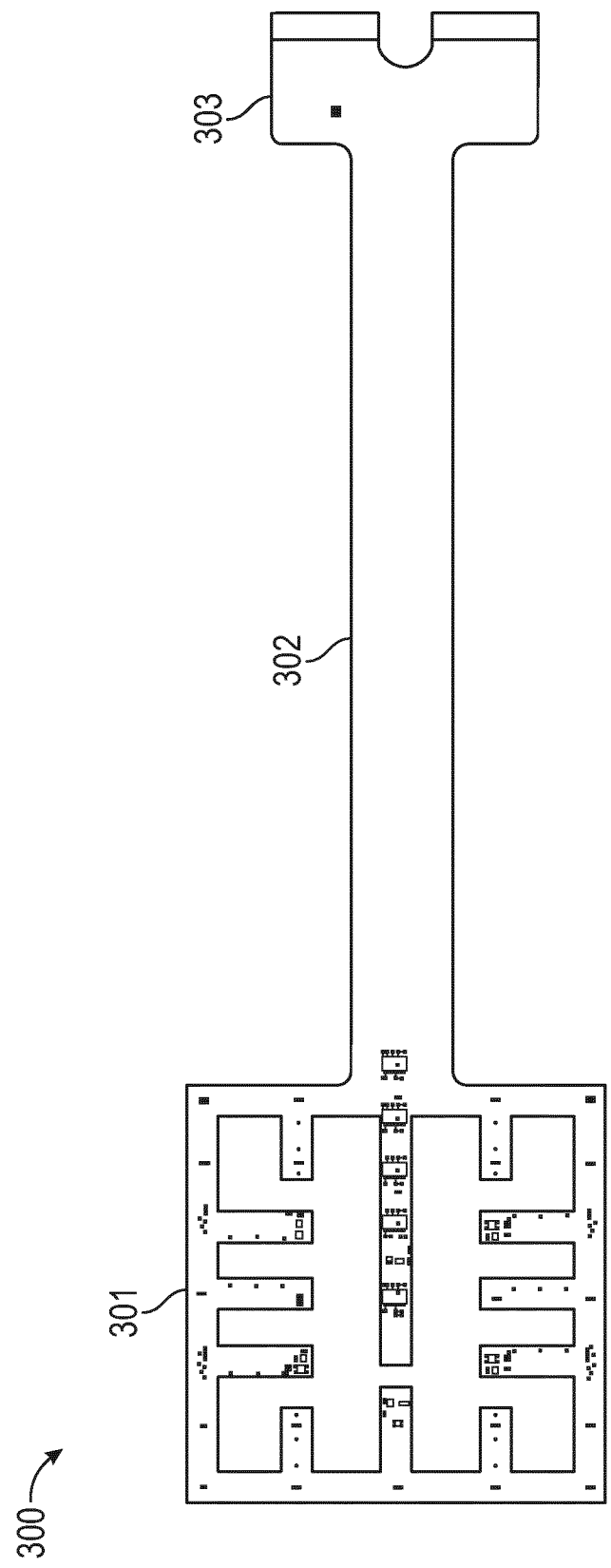
FIG. 3A illustrates a flexible sensor array including a sensor array portion, a tail portion and a connector pad end portion according to some embodiments.

In some implementations, a number of sensor technologies can be used in wound dressings or one or more components forming part of an overall wound dressing assembly. For example, as illustrated in FIGS. 2 and 3D, which depict wound dressings 250 and 320 with sensor arrays according to some embodiments, one or more sensors can be incorporated onto or into a wound contact layer, which may be a perforated wound contact layer as shown in FIG. 3D. The wound contact layer in FIGS. 2 and 3D is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing assembly or components of a wound dressing assembly, such as gauze, foam or other wound packing material, a superabsorbent layer, a drape, a fully integrated dressing like the Pico or Allevyn Life dressing, etc. In other embodiments, the sensor integrated wound contact layer may be part of a single unit dressing such as described herein.

The sensor-integrated wound contact layer can be placed in contact with the wound and will allow fluid to pass through the contact layer while causing little to no damage to the tissue in the wound. The sensor-integrated wound contact layer can be made of a flexible material such as silicone and can incorporate antimicrobials or other therapeutic agents known in the art. In some embodiments, the sensor-integrated wound contact layer can incorporate adhesives that adhere to wet or dry tissue. In some embodiments, the sensors or sensor array can be incorporated into or encapsulated within other components of the wound dressing such as the absorbent layer or spacer layer described above.

As shown in FIGS. 2 and 3D, five sensors can be used, including, for instance, sensors for temperature (such as, 25 thermistor sensors, in a 5×5 array, ~20 mm pitch), oxygen saturation or SpO2 (such as, 4 or 5 SpO2 sensors, in a single line from the center of the wound contact layer to the edge thereof, 10 mm pitch), tissue color (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and conductivity (such as, 9 conductivity contacts, in a 3×3 array, ~40 mm pitch). As shown in FIG. 3A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, or on intact skin to measure changes between the various regions. In some embodiments, the wound contact layer or sensor array can be larger than the size of the wound to cover the entire surface area of the wound as well as the surrounding intact skin. The larger size of the wound contact layer and/or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester, polyethylene naphthalate (PEN), polyetherimide (PEI), along with various fluropolymers (FEP) and copolymers, or any material known in the art. The sensor array can be incorporated into a two-layer flexible circuit. In some embodiments, the circuit board can be a multi-layer flexible circuit board. In some embodiments, these flexible circuits can be incorporated into any layer of the wound dressing. In some embodiments, a flexible circuit can be incorporated into a wound contact layer. For example, the flexible circuit can be incorporated into a wound contact layer similar to the wound contact layer described with reference to FIG. 1B. The wound contact layer can have cutouts or slits that allow for one or more sensors to protrude out of the lower surface of the wound contact layer and contact the wound area directly.

In some embodiments, the sensor-integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressings or one or more components forming part of an overall wound dressing assembly. The upper surface of the first wound contact layer and the lower surface of the second wound contact layer can be adhered together with the flexible circuit board sandwiched between the two layers.

In some embodiments, the one or more sensors of the flexible circuit board can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 3D are shown protruding out the bottom surface of the wound contact layer. In some embodiments, the SpO2 sensors can be mounted directly on a lower surface of the first wound contact layer. Some or all of the sensors and electrical or electronic components may be potted or encapsulated (for example, rendered waterproof or liquid-proof) with a polymer, for example, silicon or epoxy based polymers. The encapsulation with a polymer can prevent ingress of fluid and leaching of chemicals from the components. In some embodiments, the wound contact layer material can seal the components from water ingress and leaching of chemicals.

In some embodiments, gathering and processing information related to the wound can utilize three components, including a sensor array, a control or processing module, and software. These components are described in more detail herein.

FIG. 3A illustrates a flexible sensor array circuit board 300 that includes a sensor array portion 301, a tail portion 302, and a connector pad end portion 303 according to some embodiments. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound, such as for example in a more convenient location away from the wound.

Figure 3B:
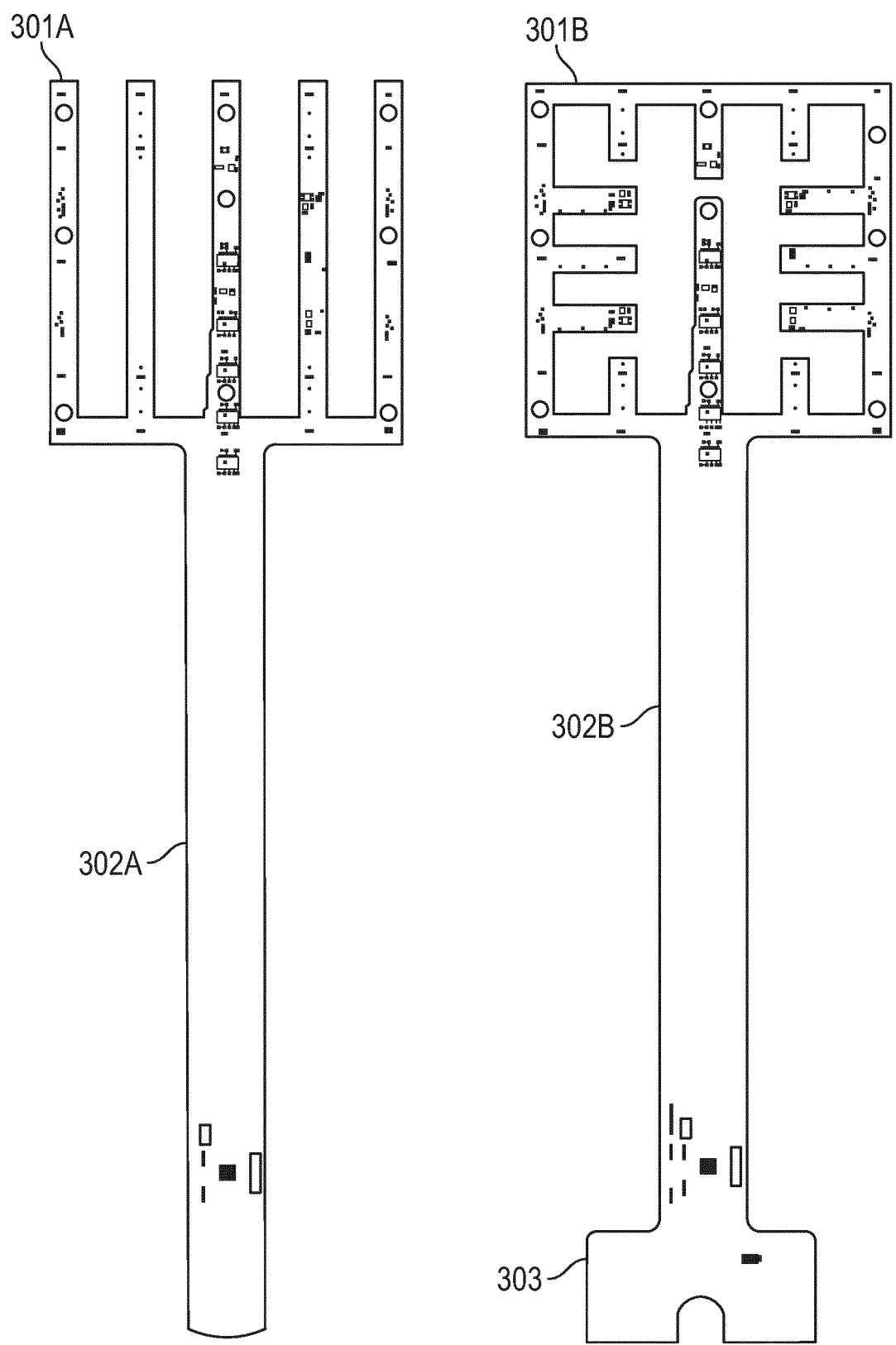
FIG. 3B illustrates flexible circuit boards with different sensor array geometries according to some embodiments.
Figure 3B:
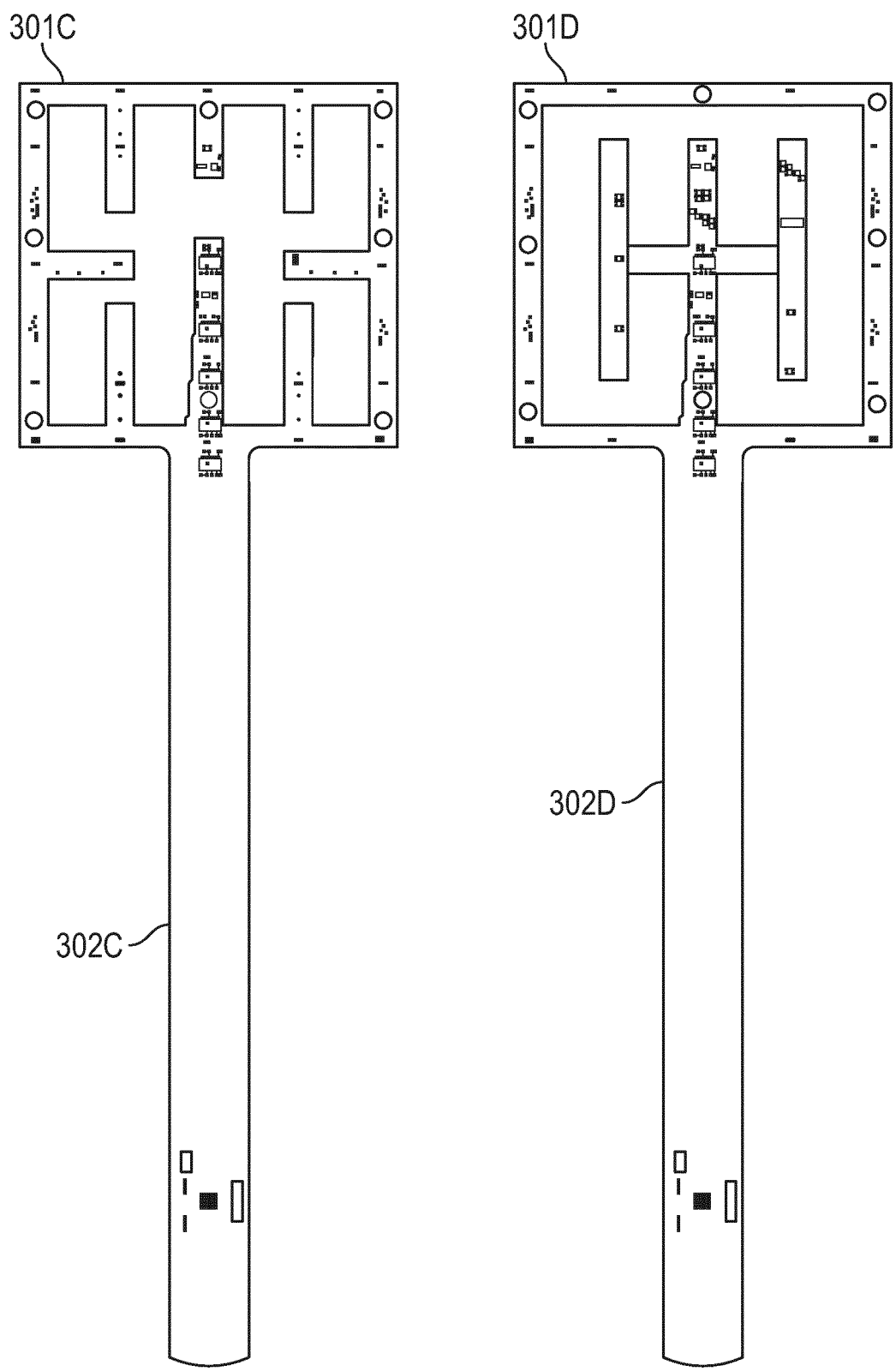

FIG. 3B illustrates embodiments of the flexible circuit boards with four different sensor array geometries 301A, 301B, 301C, and 301D according to some embodiments. The illustrated embodiments include tail portions 302A, 302B. 302C, and 302D. In some embodiments, four different sensor array geometries shown can be implemented in flexible circuits. While FIG. 3B show four different sensor array formats and configurations, the design 301B and 302B also includes the connector pads end portion 303 configured to provide electrical or electronic connection between the sponsor array 301B and a control module. One or more of the designs in 301A, 301C, or 301D can also include a connector pads end portion, such as the portion 303, to allow flexible circuit boards 301A, 301C, or 301D to communicate with a control module or other processing unit. In some embodiments, the sensor array communicates with the control module wirelessly and the tail portion may be omitted.

Figure 3C:
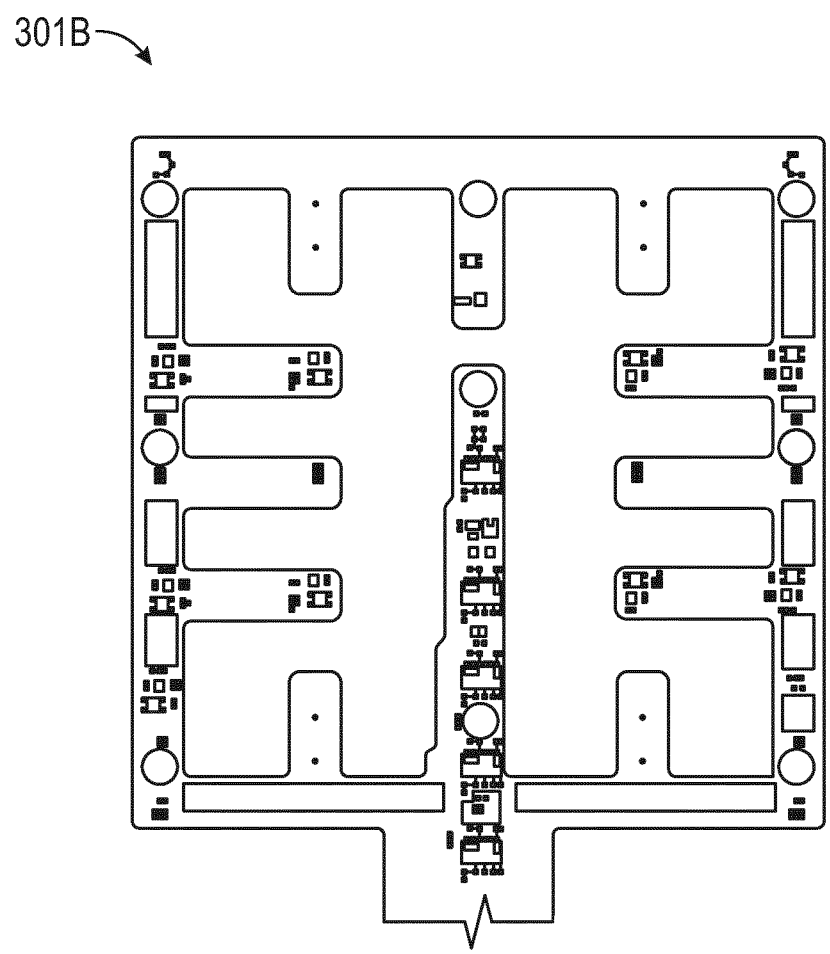
FIG. 3C illustrates the sensor array portion 301B of a sensor array shown in FIG. 3B.
Figure 3D:
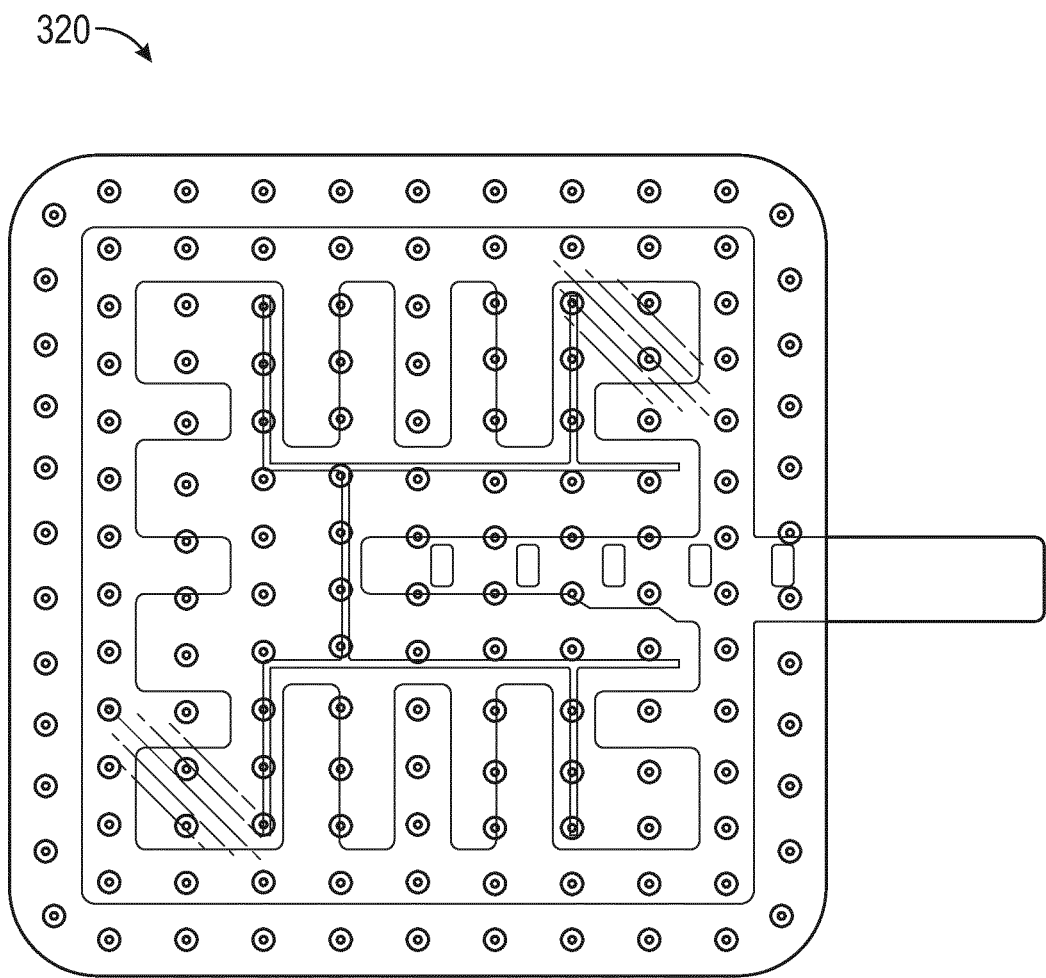
FIG. 3D illustrates a flexible sensor array incorporated into a perforated wound contact layer according to some embodiments.

FIG. 3C shows the sensor array portion 301B of the sensor array design shown of FIG. 3B in more detail. In any one or more of the embodiments of FIG. 2 or 3A-3D, the sensor array portion can include a plurality of portions that extend either around a perimeter of a wound dressing component such as a wound contact layer, or inward from an outer edge of the wound dressing component. For example, the illustrated embodiments include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 2, this allows some, and possibly a majority of the wound dressing component to be uncovered by the sensor array. For example, for a perforated wound contact layer as shown in FIGS. 2 and 3D, the sensor array portion 301 may not block a majority of the perforations in the wound contact layer. In some embodiments, the sensor array may also be perforated or shaped to match the perforations in the wound contact layer to minimize the blocking of perforations to fluid flow.

FIG. 3D illustrates a flexible sensor array incorporated into a perforated wound contact layer 320 according to some embodiments. As is illustrated, the sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

Connectivity for the sensor array can vary depending on the various sensors and sensor array designs utilized. In some embodiments, for example as shown in FIG. 3B, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, one or more of thermistors, conductivity sensors, SpO2 sensors, or color sensors can be used on the sensor array to provide information relating to conditions of the wound. The sensor array and individual sensors can assist a clinician in monitoring the healing of the wound. The one or more sensors can operate individually or in coordination with each other to provide data relating to the wound and wound healing characteristics.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. In some embodiments, an ambient sensor measuring ambient air temperature can also be used to assist in eliminating problems associated with environment temperature shifts.

Optical sensors can be used to measure wound appearance using an RGB sensor (for example, a red, green, blue, and clear (RGBC) sensor or red, green blue, and white (RGBW) sensor) with an illumination source. In some embodiments, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomise the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size or wound shape change. In some embodiments, the conductivity sensors can be used in the wound bed or on the perimeter of the wound.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some embodiments, the thermistors can be arranged in groups of five. Each thermistor is nominally 10 kΩ, and each group of five has a common ground. There are five groups of thermistors, giving a total of 30 connections. In some embodiments, there can be nine conductivity terminals. Each conductivity terminal requires one connection, giving a total of 9 connections. In some embodiments, there can be five SpO2 sensors. Each SpO2 sensor requires three connections, plus power and ground (these are covered separately), giving a total of 15 connections. In some embodiments, there can be 10 color sensors. Each color sensor comprises an RGB LED and an RGB photodiode. Each color sensor requires six connections, however five of these are common to every sensor, giving a total of 15 connections. Power and ground are considered separately. In some embodiments, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some embodiments, the sensor array can include 25 thermistor (Murata NCP15WB473E03RC), 9 conductivity terminal, 5 SpO2 (ADPD144RI), 10 RGB LED (such as KPTF-1616RGBC-13), 10 RGB Color Sensor, 10 FET, a printed circuit board (PCB), and an assembly.

A control module can be used to interface with the sensor array. In some embodiments, the control module can contain a power source, such as batteries, and electronics to drive the sensors. The control module can also log data at appropriate intervals and allow data transfer to an external computing device, such as a personal computer (PC). The control module can be customized to have various features depending on the sensors used in the sensor array and the data collected by the sensors. In some embodiments, the control module can be comfortable enough and small enough to be worn continuously for several weeks. In some embodiments, the control module can be positioned near the wound dressing or on the wound dressing. In some embodiments, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. In some embodiments, the control module can be adapted to be utilized with different sensor arrays and can enable easy replacement of the sensor array.

In some embodiments, the control module can include various requirements and combination of features including but not limited to the features listed in Table 1 below.

TABLE 1

Figure 3E:
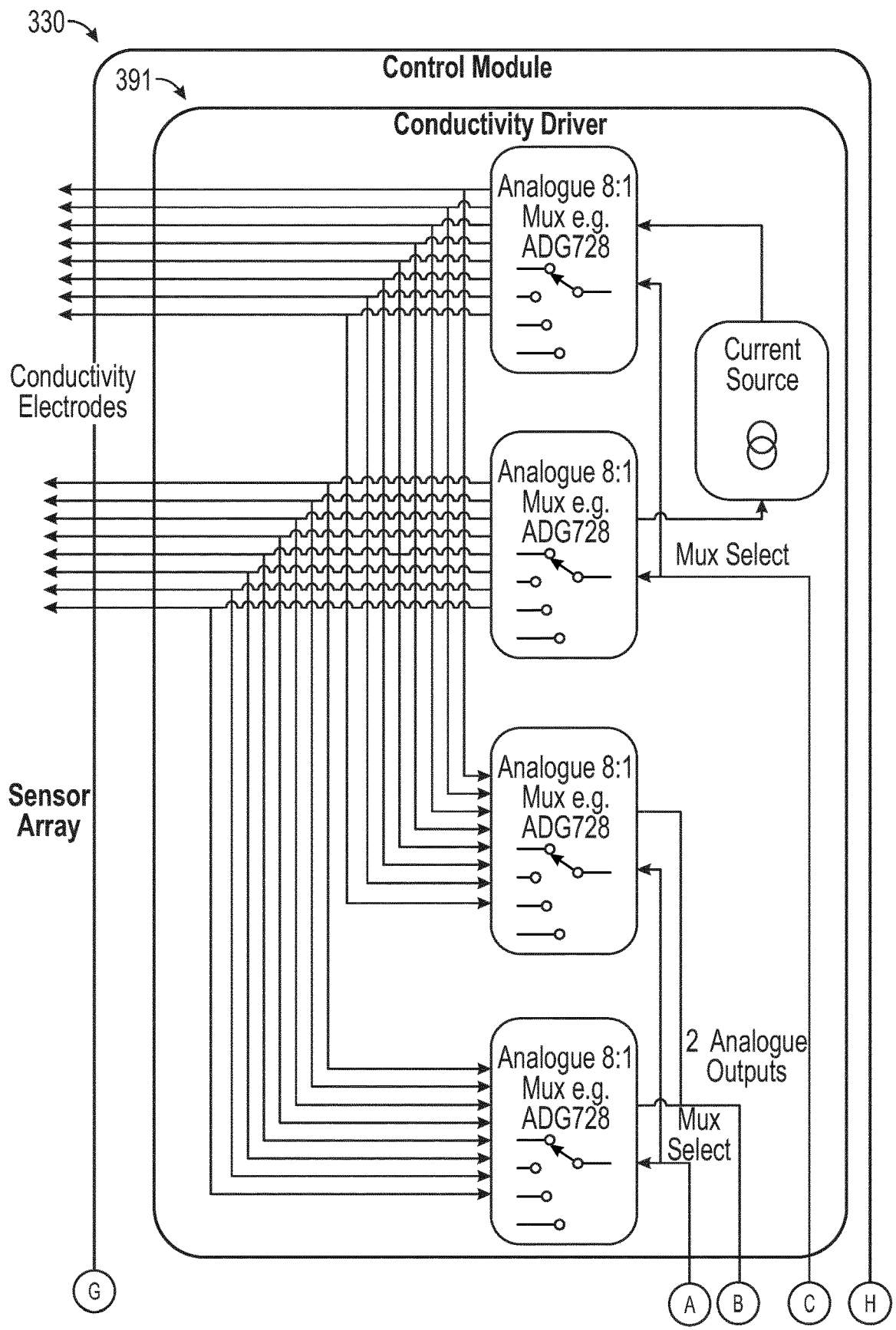
FIG. 3E illustrates a control module according to some embodiments.
Figure 3E:
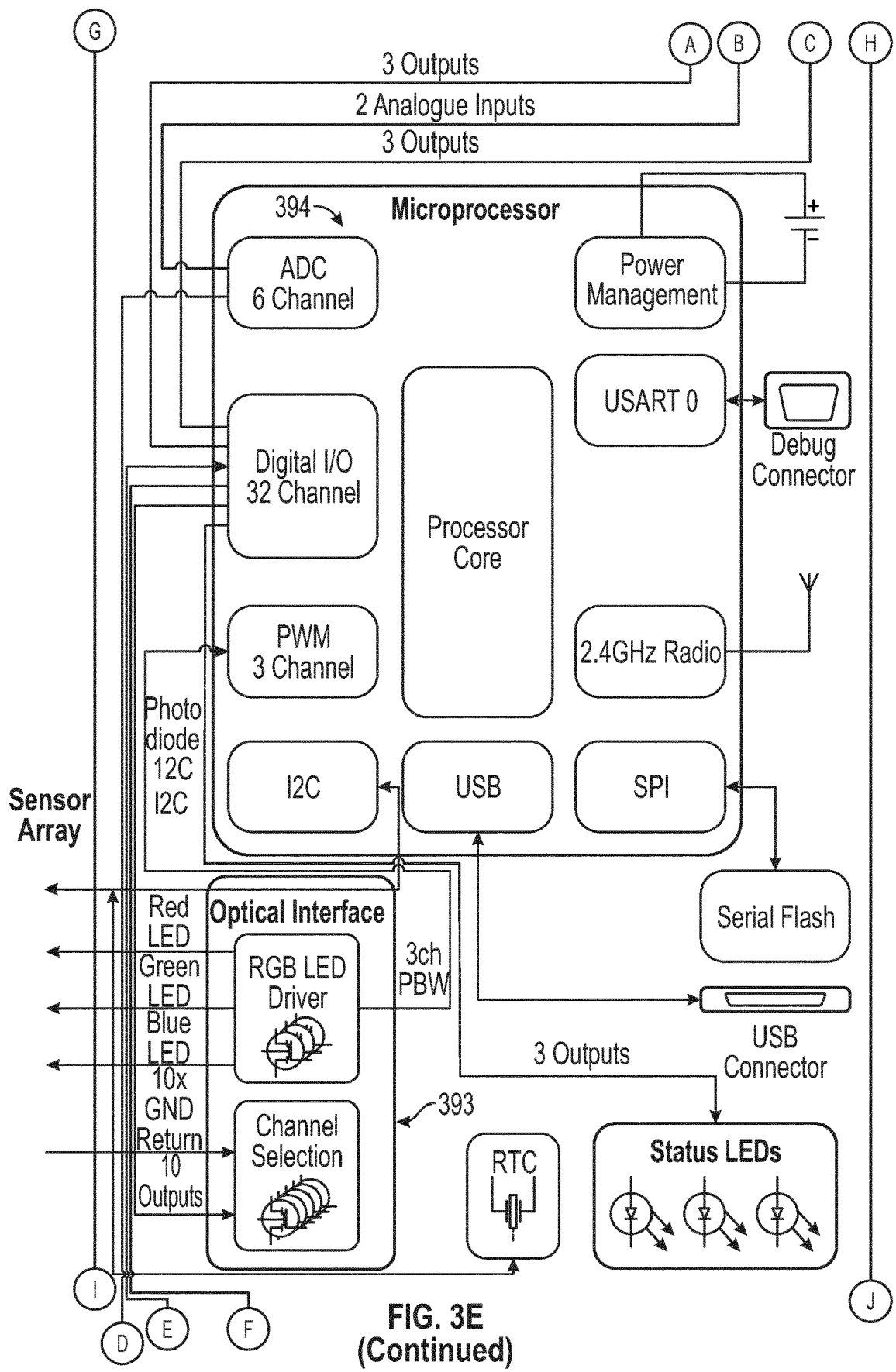
Figure 3E:
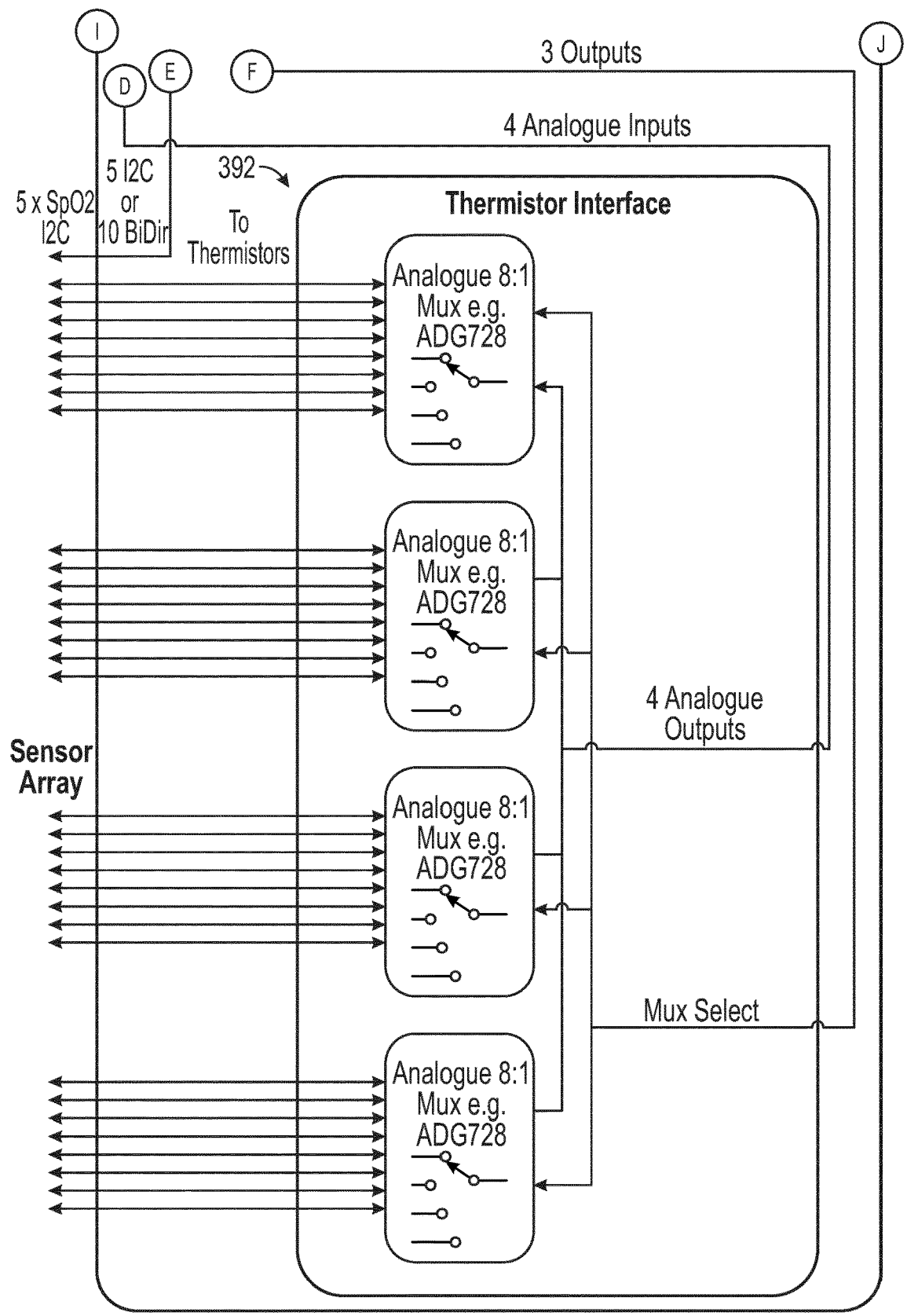

OPTIONAL FEATURES FOR CONTROL MODULE 7 day operation from a single set of batteries
28 day local, non-volatile, storage capacity
Easy to charge, or to replace battery
Wireless link to PC/tablet (such as Bluetooth)
Wired link to PC (optional, micro-USB)
Drive electronics for thermistors
Drive electronics for conductivity sensors
Drive electronics for optical sensors
Drive electronics for SpO2 sensors
Power management
Real Time Clock (RTC) to allow accurate data logging, and correlation with other measurands
Ability to change sample rates and intervals (useful for SpO2) for each sensor
Indication of status via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low FIG. 3E illustrates a block diagram 330 of a control module according to some embodiments. The block diagram of the control module includes a conductivity driver box 391 displaying features of the conductivity driver. Box 392 shows the features of the thermistor interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 3E.

In some embodiments, the microprocessor can have one or more of the following features: 2.4 GHz or another suitable frequency radio (either integrated, or external); Supplied Bluetooth software stack; SPI interface; USB (or UART for external USB driver); I2C; 3 channel PWM; 32 GPIO; or 6-channel ADC. In some embodiments, the device can require at least 48 I/O pins or possibly more due to banking limitations. Bluetooth stack typically requires ~20 kB on-board Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

In some embodiment, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051 HR can be used. Based on the initial system architecture, 8 of these will be required.

The control module can incorporate a power source, such as a battery. For example a 300 mWh/day battery can be used. For 7 days this is 2100 mWh. This could be provided by: a 10 days, non-rechargeable, ER14250 (14.5 mm diameter×25 mm) LiSOCl2 cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by host software. The software may be executed on a processing device. The processing device can be a PC, tablet, smartphone, or other computer capable of running host software. The processing device executing the software can be in communication with the control module through electrical wires or through wireless communication. In some embodiments, the software may be configured to provide access to the data held on the control module, but not to perform big-data analysis. The host software can include an interface to the control module via Bluetooth or USB. In some embodiments, the host software can read the status of control module, download logged data from control module, upload sample rate control to control module, convert data from control module into format suitable for processing by big-data analysis engine, or upload data to cloud for processing by analysis engine.

The software may be developed for PC (Windows/Linux), tablet or smartphone (Android/iOS), or for multiple platforms.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Nanosensors

In some embodiments, a wound dressing assembly can incorporate or include one or more nanotechnology-enabled sensors (also referred to as nanosensors). The nanosensors can be utilized to measure any one or more of volume, concentration, displacement and velocity, gravitational, electrical, and magnetic forces, pressure, or temperature of cells in a body. Nanosensors may be able to distinguish between or recognize certain cells at the molecular level in order to deliver medicine or monitor development to specific places in the body. Nanosensors can detect characteristics of the wound which can be used to, for instance, monitor a wound and recommend a treatment plan based on how well it is healing. A set of nanosensors can work as a collective community. For example the nanosensors can communicate as a network and can be formulated into substrates (for example, foams or wound fillers which can be placed into a wound cavity).

As described herein with respect to other sensors, nanosensors can be incorporated into an array, a string, a flexible circuit board, a matrix, a chip, etc. In some embodiments, the nanosensors can be electronically printed on, for instance, a thin, light, disposable or flexible material. In some embodiments, the nanosensors are biocompatible.

As a wound heals, it can create electric fields. In some embodiments, the nanosensors can interpret and analyze the electrical signals given off by a wound. Thus, nanosensors can detect or precisely measure of those fields over time, thereby non-invasively tracking a healing process of a wound. In some embodiments, the nanosensors can track how fast or how well a wound is healing. In some embodiments, the nanosensors can accelerate wound healing. In some embodiments, the wound dressing assembly can be utilized to monitor progression of healing of a wound.

In some embodiments, the nanosensors can communicate (for instance using incorporated antennae) with one or more other sensors or other communication device, such as a remote controller. The nanosensor data can be wirelessly transmitted and analyzed.

Sensor Placement

Accurate placement of a sensor or a sensor array can be important to effective treatment of a wound or to effective data gathering. For example, various locations in or around wound can have drastically different characteristics. Without knowing where a sensor is located (for example, relative to the wound, other sensors, the patient, etc.), measured or calculated data can be misleading or inaccurate, thereby making it difficult to provide effective treatment to a patient. In some embodiments, one or more techniques are utilized to assist in increasing the accuracy of the sensor data. For example, one or more techniques are provided for reducing the chances of imperfect or incorrect placement. In addition, one or more techniques are provided for increasing the accuracy of sensor data despite imperfect or incorrect placement. Similarly, one or more techniques are provided which do not require specific, precise placement of sensors to gather accurate information.

The position or orientation of one or more sensor strings, sensor strips, sensor arrays, or sensor matrices (generally referred to as sensor package), wounds, wound dressings, wound fillers, wound dressing assemblies, etc. can be tracked or determined and may be utilized to limit orientation errors. For example, alignment or orientation considerations may be taken with respect to how a sensor package is placed in or onto the wound (or periphery of the wound) to ensure that when the sensor package is installed or replaced, its orientation in each case is known. This can be necessary to co-reference and cross-reference data. In addition, the position or orientation data can be utilized to assist in the placement (for example, initial placement or subsequent adjustments) of a wound dressing or sensor package to lessen the likelihood of imperfect placement. Sensor data or sensor functionality can be modified based on the position or orientation data, for example, in order to increase the accuracy of sensor data despite imperfect placement.

A sensor package can be utilized to limit orientation errors. For example, it may prove difficult to place a single sensor in a desired location because, for instance, the sensor may be small or difficult to orient correctly. A sensor package, on the other hand, can be easier to orient because, for example, the increased size or potential for orientation markers, as described herein.

Sensors or sensor package can be incorporated into or encapsulated within a wound dressing or wound packing material. For example, the sensors may be stitched into or otherwise permanently or semi-permanently attached to gauze or durafibre or one or more layers of the wound dressing. As another example, the sensors may be mounted onto foam protrusions which fit into wound. Still, in another example, a sensor or sensor package may be deployed into an expandable matrix, foam or other material which fills the wound. In some embodiments, the one or more sensors can be utilized to monitor progression of healing of a wound.

In some embodiments, a one or more sensors can be positioned on or supported by a substrate. The substrate can be flexible or substantially flexible. The substrate can be part of a wound contact layer. Additional details of sensors positioned on a substrate are disclosed in International Patent Application No. PCT/EP2018/059333, filed on Apr. 11, 2018, which is hereby incorporated by reference in its entirety.

Alignment Features

Figure 4C:
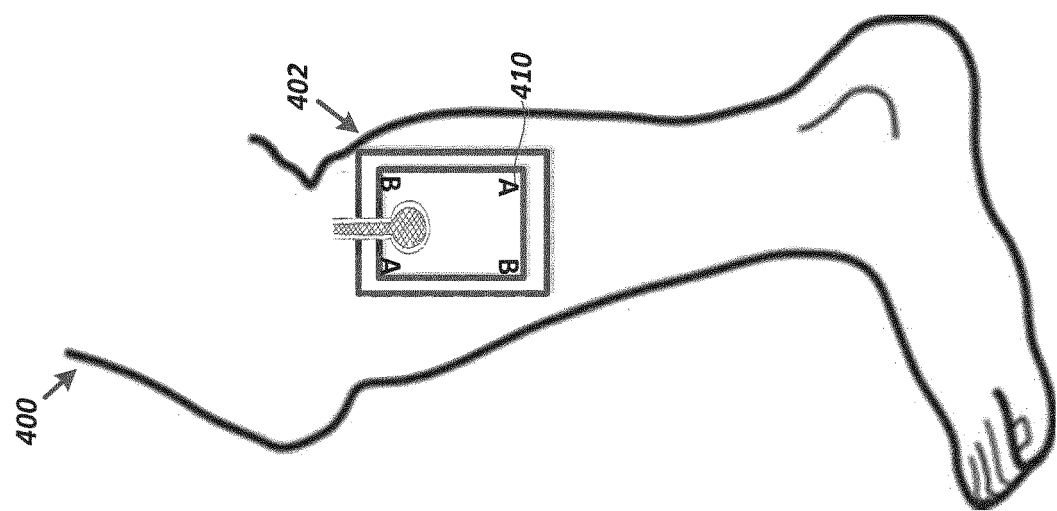
FIGS. 4A-C illustrate embodiments of a monitoring or therapy system having a plurality of alignment features for assisting in proper placement of a wound dressing on a wound.
Figure 4B:
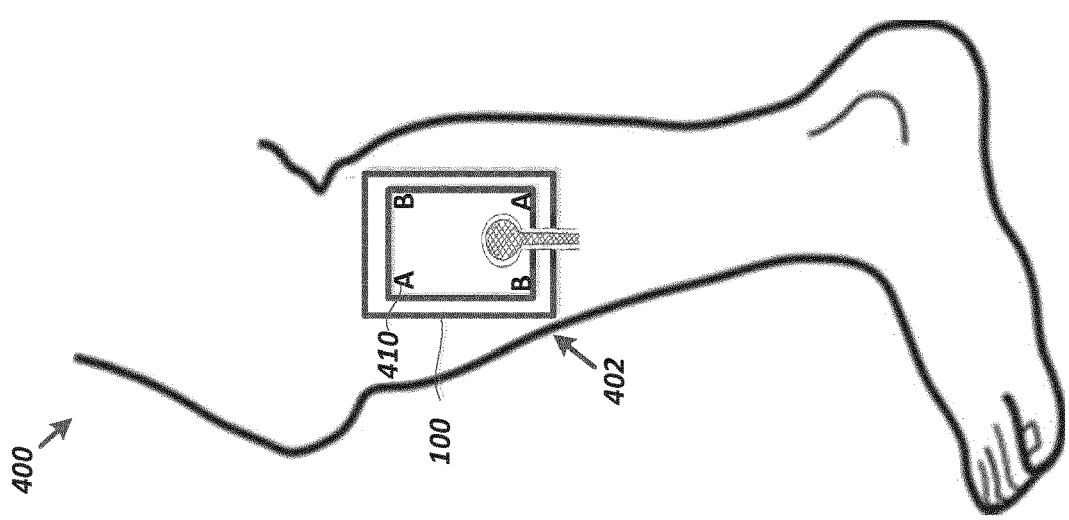
Figure 4A:
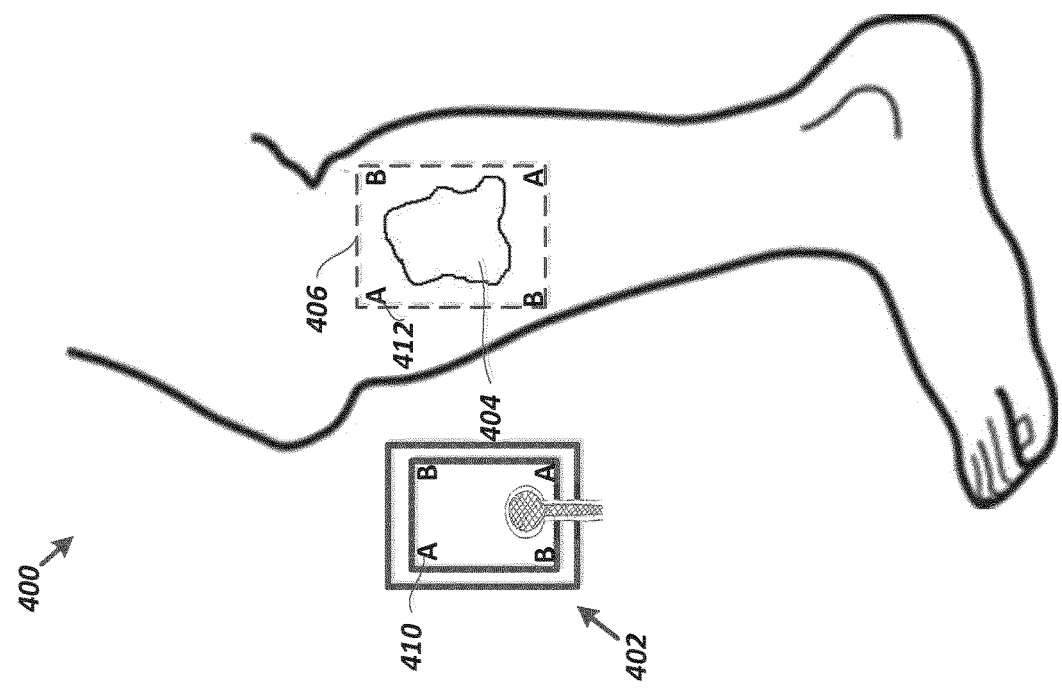

FIGS. 4A-C illustrate diagrams of a monitoring or therapy system 400, such as a negative pressure wound therapy (NPWT) system, having a plurality of alignment features 406, 410, 412 for assisting in proper placement of a wound dressing 402 in or on a wound 404 according to some embodiments. The system 400 includes a wound dressing 402 which can be any wound dressing as described herein, such as wound dressing 100 of FIGS. 1C-1D. In addition, the system 400 can include a pump (not shown) connected to the wound dressing, as described herein. The one or more alignment features 406, 410, 412 can be included in or on the wound dressing or in or on a periphery of the wound. The one or more alignment features 406, 410, 412 can help reduce a likelihood of an imperfect or incorrect placement of a wound dressing 402 on the wound 404.

FIG. 4A illustrates a wound dressing 402 prior to its placement in, on or around a wound 404. FIGS. 4B-4C illustrate a properly positioned wound dressing 402 in, on, or around the wound 404 using one or more alignment features 406, 410, 412. As illustrated, the alignment features include an alignment ring 406 and orientation features 410, 412. However, it should be noted that one or more other alignment features can be used in addition or alternatively. For example, other alignment features can include a full or partial image or diagram of a patient. For instance, the wound dressing can be correctly oriented when the orientation of the patient in the diagram matches the orientation of the patient. In addition, alignment features can include corner indicators which indicate an area of location for placement of the wound dressing corners. Alignment features can also include anatomical feature indicators. For instance, an arrow or other directional element is on the wound dressing and will point to a particular location (for example, a patient's left foot) when positioned correctly. In some embodiments, alignment features can also include a pattern or other marking which can indicate a correct orientation of the wound dressing. For example, the alignment features can include a plurality of blocks placed in a corner of the wound dressing. The wound dressing is oriented correctly when the blocks are in the top left corner.

The alignment features can include an orientation indicator, such as an accelerometer, orientation sensor, gravity sensor or level. For example, the alignment feature can include a sealed chamber or bubble with fluids of different densities (e.g. air bubble in saline). The orientation or position of the fluids can indicate the orientation of the wound dressing. The one or more alignment features can assist in guiding a patient or caregiver in the placement or replacement of wound dressings, wound filling material, sensors, or sensor packages. As described herein, one or more sensors can be integrated into a sensor package, a wound dressing, wound filling material, etc. Similarly, a sensor package can be integrated into a wound dressing or wound filling material.

An alignment ring 406 can be configured such that when the wound dressing 402 is aligned (for example, fits within, matches, or corresponds) with the alignment ring 406, the wound dressing or any sensors integrated in the wound dressing are properly positioned. The alignment ring 404 may be semi-permanently attached to or printed in or around the wound 402 to allow wound dressing 401 to be accurately placed or replaced in a desired position. The alignment ring can be any semi-permanent or permanent visual or other indicator which can assist in the placement of the wound dressing 402. For instance, the alignment features can be a temporary tattoo, ink (e.g. invisible ink), tape, sticker, anatomical feature, etc.

In some cases, the system 400 can include a wearable system configured to present two-dimensional (2D) or three-dimensional (3D) virtual images to a user. For example, in addition or alternatively to including a physical alignment ring 406 (which may be semi-permanently attached to or printed in or around the wound 402), the wearable system can present the alignment ring 406 as a virtual image to the user. Similarly or alternatively, any one or more of the other alignment features described herein can be presented as virtual images to the user The images can be still images, frames of a video, a video, in combination or the like. The wearable system can include a wearable device that can present a virtual reality (for example, presentation of digital or virtual image information without transparency to other actual real-world visual input), augmented reality (for example, presentation of digital or virtual image information as an augmentation to visualization of the actual world around the user), or mixed reality (for example, presentation related to merging real and virtual worlds to produce new environments where physical and virtual objects co-exist and interact in real time) environment, alone or in combination, for user interaction. The wearable device can be a head-mounted device (HMD) or other device.

Although the alignment ring 406 is illustrated having a rectangular shape, it will be appreciated that the alignment ring 406 can take any shape including other shapes such as rectangular, circular, oval, etc. In some embodiments, the shape of the alignment ring advantageously matches the shape of the wound dressing 402 to allow for easy and accurate placement. However, in some instance, the shape of the alignment ring 406 is different from the shape of the wound dressing 402.

In some embodiments, other alignment features are utilized in addition to or instead of the alignment ring 406. For example, an indicator which indicates the desired position of an edge, corner, or sensor can be utilized. As a non-limiting example, the alignment features can include two or more corner indicators, such that when corners of the wound dressing 402 are positioned at the corner indicators, the wound dressing is accurately placed. As another example, the alignment features can be included on the wound dressing 402 and can correspond to an anatomical feature of the patient. For example, the wound dressing 402 can include an arrow designed to point at an anatomical feature (for example, a patient's head), when properly aligned.

In some embodiments, a patient, caregiver, computer guided apparatus, etc. can draw, place, stick, or otherwise position one or more alignment features on a wound dressing, sensor, sensor package, or a patient's body to assist in the positioning of the wound dressing or sensors. In other instances, the alignment features can be projected (such as with a light source) or seen using a form of virtual or augmented reality.

In some instances, the alignment features are determined prior to placement of the wound dressing 402. For example, a computing system or physician can determine where an alignment ring should be placed on a patient based at least in part on known sensor positioning within the wound dressing. As another example, the position or orientation of the alignment features can be determined based at least in part on the size, location, shape, depth, etc. of the wound. Alternatively or in addition, the position or orientation of the alignment features can be determined based at least in part on the type(s) of sensors to be used in the wound dressing.

The alignment features can be determined after the wound dressing or sensors have been attached to or placed on the patient for a first time. For example, in some instances, wound dressings may require periodic replacement. In examples such as these, the wound dressing can be initially placed in or on a wound without utilizing any alignment features. For instance, as described herein, a wound dressing or sensor may not require specific placement in or on the wound. Instead, the individual sensor components may have a means of registering their position with respect to each other in order to understand their position within a wound. However, when the wound dressing is replaced with a new wound dressing, it can be desirable (for example, for data accuracy or consistency) to place the new wound dressing in the same or substantially same location as the old wound dressing. Accordingly, in some embodiments, the alignment features can be determined after the initial placement and position registering of the sensors. For example, an outline or other indication of the wound dressing can be marked on the patient's body. Subsequently, when the wound dressing is replaced, a new wound dressing can be accurately placed using the alignment features.

In some embodiments, to further reduce a likelihood of imperfect or incorrect placement, a wound dressing or sensor package may be at least partially rotationally symmetric, such that the accuracy of the sensors will not be impacted by rotational misalignment. In some embodiments, rotationally symmetric means that the sensors are rotationally symmetrically positioned in the wound dressing or sensor package such that, when rotated by a certain degree, sensors of the same type remain positioned in the same locations. For example, wound dressing 402 illustrated in FIGS. 4A-4C includes orientation marks (A, B, B, A) 410 which correspond to orientation marks (A, B, B, A) 412 at the wound 404. As illustrated by FIGS. 4B and 4C, because the wound dressing 402 is rotationally symmetric, the wound dressing can be accurately positioned despite whether it is oriented as illustrated in FIG. 4B or as illustrated in FIG. 4C. Note that orientation marks 410 and 412 are matched (for example, A corresponds to A, B corresponds to B, etc.) in both orientations.

Position or Orientation of Sensors

A system (such as, the system 400) can utilize a positioning sensing device to determine or track the position or orientation of sensors or other objects of interest, estimate movement, position, or location of the sensors, wound, patient, or the like. For example, the system can include sensors which can continually, or repeatedly, report or receive position or orientation data to, for instance, one or more other sensors. In addition or alternatively, the system can utilize sensor packages in which the position or orientation of each sensor on sensor package is known or can be determined, and a single or a few sensors can be used to register the location of the sensor package.

As described herein, position or orientation (also referred to as emplacement) considerations may be taken with respect to how one or more sensors (or a wound dressing) are placed in or onto the wound to ensure that when the one or more sensors are installed or replaced, their orientation in each case is known. The term emplacement as used herein may refer to, without limitation, position or orientation or any other appropriate location information. These placement considerations can be desired, for instance, to co-reference and cross-reference data such that the position of each sensor relative to a wound or a point or reference can be determined. For example, the individual sensor components may have a means of registering their position with respect to each other in order to understand or record position on, around, or within a wound.

The position or orientation of a sensor, sensor package, or wound dressing can be tracked or determined using a variety of techniques. For example, one or more emplacement sensors can be used or integrated into a sensor package, wound dressing, etc., and a positioning sensing device (sometimes referred to as a position or positioning sensing unit) can track or otherwise determine a position or orientation of the one or more emplacement sensors within a tracking area. The positioning sensing device can provide positioning data to a processor, such as a processor of a NPWT system or a remote processor, which can co-reference or cross-reference data from other sensors. Alternatively, a processor can co-reference or cross-reference received emplacement data with known emplacement data (such as the position or orientation of sensors in the sensor package) to determine additional emplacement information. In some cases, the one or more emplacement sensors could include one or more capabilities. For example, the one or more emplacement sensors can include an orientation sensor such as an accelerometer, gyroscope, or magnetometer, such that it can output an inertial measurement unit (IMU).

As a non-limiting example, one or more emplacement sensors can be communicatively coupled to the positioning sensing device, such as a position sensing unit. The positioning sensing device can be part of a wound dressing or it can be a separate component. The positioning sensing device can be used to determine the emplacement of the emplacement sensor or a set of sensors (for example, a sensor array). For example, the positioning sensing device can determine the pose of the one or more emplacement sensors relative to a room coordinate system. The pose and the room coordinate system can then be utilized to determine a pose of other sensors. The positioning sensing device can determine the emplacement of one or more sensors, the wound dressing, a point of reference, or the like using various techniques. For example, the positioning sensing device can utilize echo location, ultrasound, sonar to locate the sensors, wound, wound dressing, area of interest, point of reference, etc. In addition or alternatively, the positioning sensing device can utilize Global Positioning System (GPS), radio-frequency identifier (RFID) technology, imaging (for example, an external video camera), radio frequency sensing, positioning tracking or the like to locate the sensors, wound, wound dressing, area of interest, point of reference, etc.

In some embodiments, the positioning sensing device can include one or more sensing devices such as the HiBall tracking system, a GPS device, an RFID device, a RF sensor, an antenna, ultrasound, sonar device, echo location device, or a signal emitting device that would allow for tracking of the emplacement of the one or more emplacement sensors. In some embodiments, a positioning sensing device can be affixed to a wound dressing. The wound dressing assembly can be tracked by the positioning sensing device. A room coordinate system reference can also be tracked by the position sensing unit in order to determine the emplacements of the sensors or the wound dressing with respect to the room coordinate system. In addition or alternatively, the emplacements of one or more sensors or the wound dressing can be determined relative to a point of reference, such as a datum, a wound, a patient's body part, or the like. In some embodiments, the wound dressing can also include or have coupled thereto one or more accelerometers, which can also be used to estimate movement, position, and location of the wound, patient, etc.

As another example, the positioning sensing device can include a signal emitting device. The signal emitting device can include a radio-frequency identifier (RFID). In such embodiments, the signal emitting device can use GPS coordinates of the one or more tracking units or can, for example, triangulate the radio frequency signal being emitted by the RFID associated with the one or more tracking units to determine an emplacement of the wound dressing, sensors, etc. Alternatively or in addition, the sensor package may register itself with electromagnetic tags (e.g. RFID tags) placed on or near the patient that allow the sensor package to define its position and orientation with respect to the tags.

As another example, the positioning sensing device can include an imaging device, such as an optical sensor, camera, or scanner. In examples such as these, the imaging device can read, scan, image, records, or gather information from an alignment feature associated with the wound or a wound dressing. For example, one or more alignment features can be printed onto a surface of the wound dressing. The imaging device can be configured to determine a position or orientation of the wound dressing (or a wound, body part, etc.) based at least in part on the alignment feature. For example, the imaging device can image the alignment feature and can determine an angle of the alignment feature or the dressing relative to the positioning sensing device. In addition or alternatively, the imaging device can determine a relative size of the elements in an image or video of the imaging device. In addition or alternatively, the imaging device can determine a position or location of an alignment feature on or proximate to the wound dressing. Based on the or more characteristics of the alignment features, such as a code, distances, skew, parallax, or the like, the system can determine an emplacement of one or more sensors, points of interests, wound dressings, wounds, or the like. The determined emplacement can be an absolute emplacement or an emplacement relative to a point of reference, such as an area of interests, the wound, the wound dressing, a sensor, a body part of the patient or the like.

As another example, the system can determine a position or orientation of the wound or the wound dressing based at least in part on the position or orientation of the point of reference. The determined position or orientation can be an absolute position or a relative position (for instance, relative to the wound, the wound dressing, an object, or a particular body part of the patient). For example, the sensors can be a fixed shape or string. By locating the point of reference, which can include one or more of the sensors, the emplacement of one or more of the other sensors can be determined. In other words, known emplacement relationships between sensor, the wound dressing, the point of reference or the like can be utilized to determine the emplacement of one or more sensors, the wound dressing, etc.

The wound dressing can be associated with a point of reference. For example, a point of reference can be attached to or embedded in the wound dressing. Further, the point of reference can have known emplacement relationships between the wound dressing or one or more various sensors of the wound dressing. For example, point of reference can be a known distance from one or more sensors (for example, sensors within the wound dressing). The point of reference can be a sensor, such as an emplacement sensor. Alternatively, the point of reference can be a point, line, plane, hole, set of holes, object, or other non-sensor. A positioning sensing device can track or determine an emplacement of the point of reference, and based at least in part on the emplacement of the point of reference, the emplacement of one or more of a wound dressing, one or more sensors, an area of interest, or the like can be determined. In some cases, the system can include more than one point of reference and the positioning sensing device can track or determine an emplacement of each of the points of reference.

In addition or alternatively, the point of reference can be remote from the wound dressing. For example, the point(s) of reference can be at a known location on the body, a known distance from a portion of the body, or known distance from a wound. In some cases, the point of reference can be a positioning sensing device. The point of reference determine an emplacement of the wound dressing, an area of interest, or one or more sensors relative to the position or orientation of the point of reference. For example, one or more of the point or reference or the individual sensor components can be configured to register their position with the point of reference(s) to understand or record emplacement of the sensors or wound dressing on, around, or within a wound.

In some embodiments, the emplacement of one or a few sensors is tracked or determined, and known relationships are used to determine other emplacement data (for example, emplacement data of other sensors, the wound dressing, the wound, the patient, etc.). As described herein, one or more sensors can be incorporated into a sensor package such as a sensor string, a sensor strip, a sensor array, a sensor matrix, or a flexible circuit board. Alternatively or in addition, one or more sensors can be incorporated into a wound dressing or wound filler. The position of the sensors in the sensor package, wound dressing or wound filler may be known and relationships between other sensors, wound location, etc. can be determined.

A system, such as a negative pressure wound therapy (NPWT) system, can determine the emplacement of a first sensor and then, based at least in part on the determined placement of the first sensor and a known relationship between the first sensor and other sensors, can determine an emplacement of the other sensors. In addition or alternatively, the system can determine an emplacement of the entire sensor package and use the emplacement data of the sensor package, as well as a known relationship, to determine the emplacement of one or more sensors on the sensor package.

In some embodiments, the system can include a point of reference that serves as a reference for determining a position or orientation of one or more sensors, a sensor package, a wound, or the like. For example, a system can determine the emplacement of the point of reference or the emplacement of one or more sensors relative to the point of reference. Based at least in part on the emplacement of the point of reference, the system can determine an emplacement of one or more sensors, for example, relative to the point of reference or relative to the wound. The point of reference can be a sensor, point, line, plane, hole, set of holes, or the like.

In some embodiments, the emplacement of several or all the sensors can be tracked or determined. In some instances, the system can determine the emplacement of each sensor using more than one technique described herein (for example, tracking the sensor, determining based on a known relationship, etc.). The system can suitably arbitrate between emplacement determined using multiple techniques and can determine if an emplacement is perceived to be inaccurate or unreliable.

Figure 5:
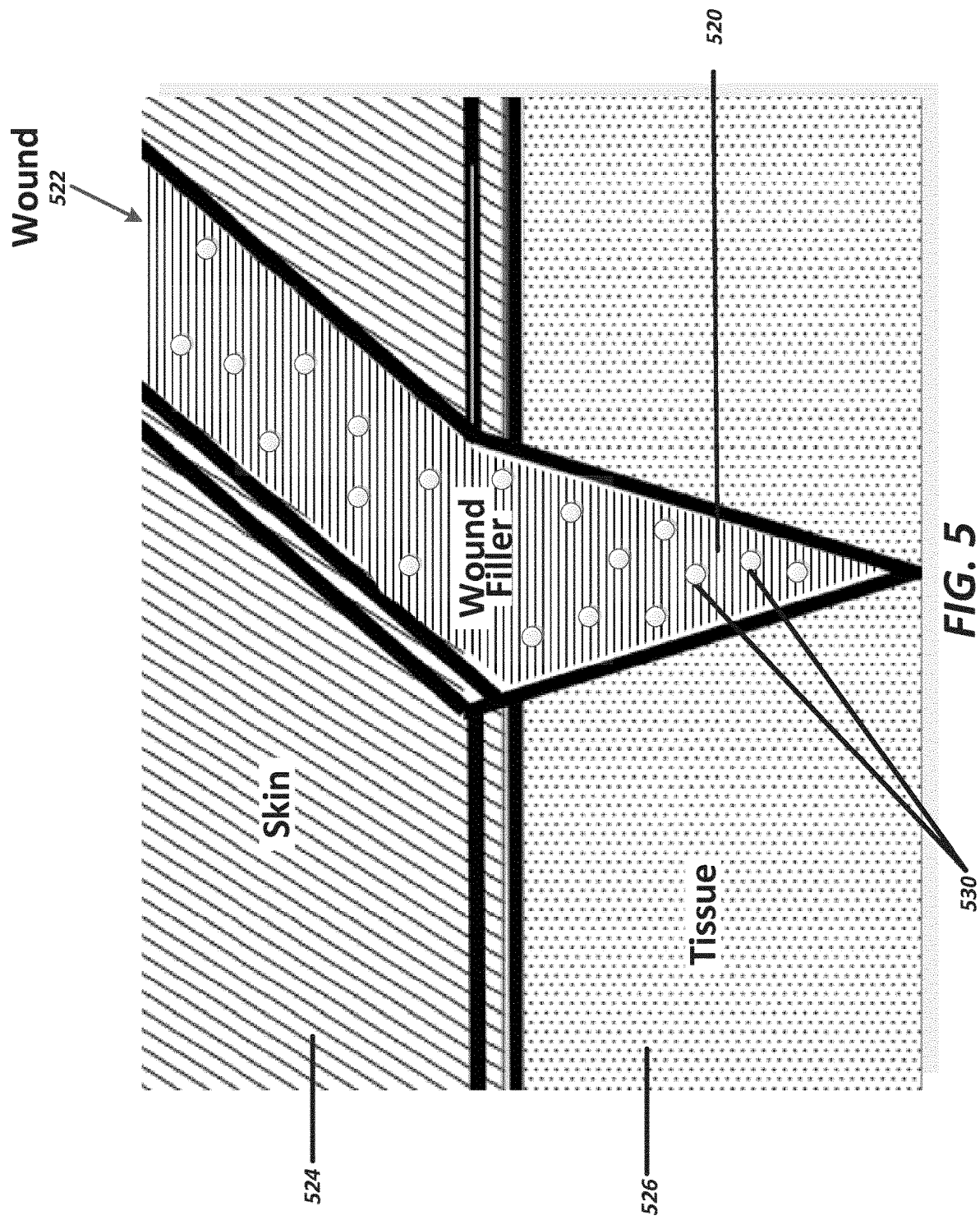
FIG. 5 illustrates a cross section of a wound packed with wound filler material having a plurality of incorporated sensors or sensor packages according to some embodiment.

FIG. 5 illustrates a cross section of a wound 522 packed with wound filler material 520 (or wound filler) having a plurality of incorporated sensors 530 or sensor packages, according to some embodiments. The wound filler material can be any material as described herein including an expandable foam or matrix which can be configured to fill the wound. The sensors 530 in the wound filler material 520 can be utilized in conjunction with sensors incorporated in a wound dressing (such as those described with respect to FIGS. 4A-4C) to provide data relating to the wound or other physiological or health data relating to the patient. Alternatively, the sensors 530 can be used exclusively to provide wound data. Still, in other examples, the sensors 530 can communicate with one or more sensors or components outside of the wound.

In some embodiments, specific placement of the sensors 530 is not required. For example, one or more sensors 530 can be incorporated into the wound filler material 520 and the wound filler material 520 can be inserted into the wound. The position or orientation of the one or more sensors 530 can be determined using one of the methods described herein. In some embodiments, the sensors 530 are positioned in the wound filler material 520 such that the position or orientation is known. For example, the sensors 530 can be positioned in a pattern and the wound filler 520 can be of a certain consistency or density such that the sensors 530 would not move while the wound filler is inserted into the wound cavity 522.

Figure 6A:
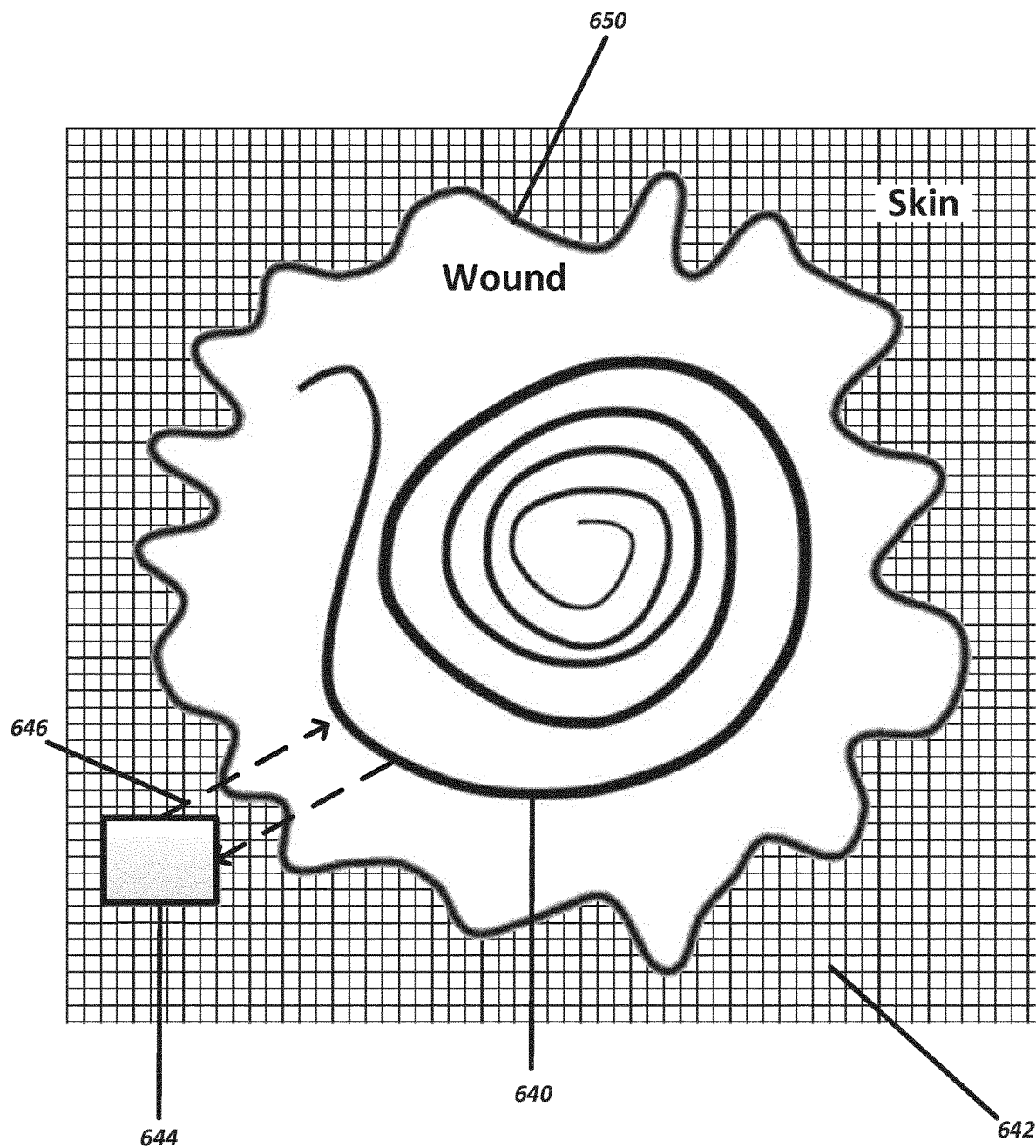
FIG. 6A illustrates a system having a strip of sensors positioned within a wound, according to some embodiments.

FIG. 6A illustrates a system having a string or strip 640 of sensors positioned within a wound 650, according to some embodiments. In some implementations, the placement of the strip 640 can require specific placement such that it should be placed by a physician or other qualified personnel. Alternatively, in certain cases, the strip 640 may not require a specific placement, and the strip 640 may be placed by any individual, such as a physician, nurse, caregiver, or the patient. In some embodiments, the strip 640 of sensors may not be a strip, but is instead another sensor package or a plurality of individual or coupled sensors.

The system can include a component 644 which can reside outside the wound, such as on the skin 642 (for example, the skin at the wound) or in a wound dressing, and can communicate 646 with the sensor strip 640. In some embodiments, the position or orientation of the component 644 can be a known input of the system. As such, the position of the component 644 and be utilized to determine the position or orientation of the sensor strip 640 or specific sensors of the strip. The component 644 can be a position sensing unit or any other positioning or locating module described herein.

The position or orientation of a sensor, sensor package, wound dressing, etc. can be determined using a camera or other recording device. For example, one or more pictures or videos may be taken of the wound prior to the filling of the wound filling or packing material, after the filling of the wound packing material, after the placement of the sensors, or after the placement of the wound dressing. The images can allow the orientation of the sensors, wound dressing, etc. to be calculated after placement. In some embodiments, an image of a wound or dressing can be utilized to determine or assign data integrity to data output from sensors of the wound dressing.

Figure 6B:
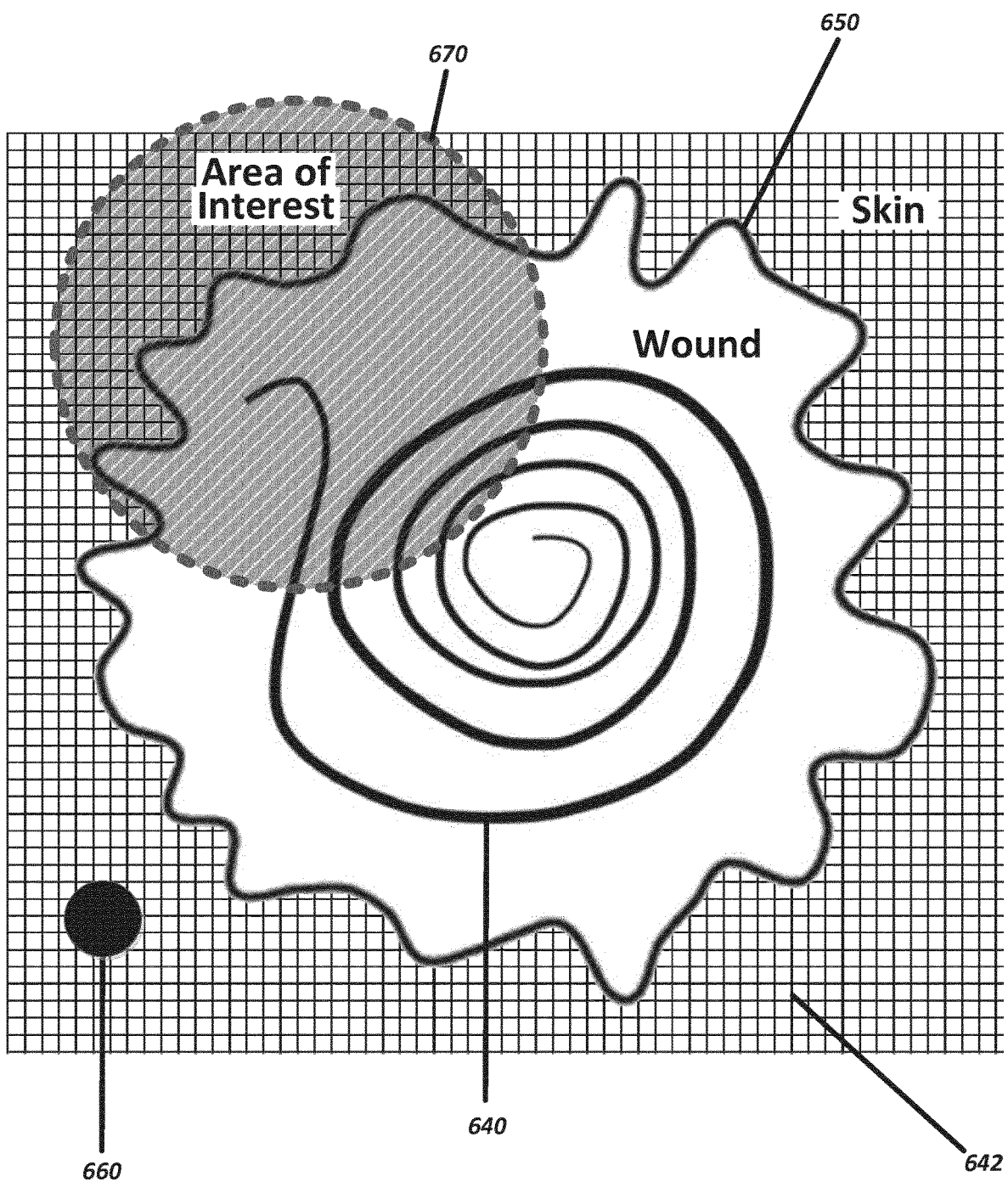
FIG. 6B illustrates a system having a strip of sensors positioned within a wound, according to some embodiments.

FIG. 6B illustrates a system having a string or strip 640 of sensors positioned within a wound 650, according to some embodiments. In addition, FIG. 6B illustrates a point of reference 660 (sometimes referred to as a datum point) and an area of interest 670.

The point of reference 660 can include a sensor, such as one or more emplacement sensors. In addition or alternatively, the point of reference 660 may not be a sensor. For example, the point of reference 660 can be a passive datum. In some cases, information associated with the point of reference 660 can be co-referenced or cross-referenced such that the position of each sensor can be determined. For example, one or more of the individual sensor components can be configured to register their position with respect to each other in order to understand or record position on or within a wound. In some cases, the point of reference 660 can have known relationships. For example, point of reference 660 can be a known distance from one or more sensors (for example, sensors within the wound dressing). In addition or alternatively, the point of reference 660 can a known distance from a portion of the body or at a particular location on the body or on the wound dressing.

In some cases, the system can determine a position or orientation of the wound or the wound dressing based at least in part on the position or orientation of the point of reference. The determined position or orientation can be an absolute position or a relative position (for instance, relative to the wound, the wound dressing, an object, or a particular body part of the patient). For example, the sensors can be a fixed shape or string. By locating the point of reference, which can include one or more of the sensors, the emplacement of one or more of the other sensors can be determined. In other words, known emplacement relationships between sensor, the wound dressing, the point of reference or the like can be utilized to determine the emplacement of one or more sensors, the wound dressing, etc.

In some embodiments, the system can monitor an area of interest 670, which can be associated with the wound 650. For example, the area of interest 670 can be a portion of the wound 650 of a portion of the periphery of the wound 650. The area of interest 670 can be monitored at a particular moment in time (for example, a single measurement) or over a period of time (for example, many measurements). For example, it can be advantageous to monitor an area of interest 670 throughout the duration of the healing time of the wound 650.

However, in some cases, throughout the duration of healing of the wound, it can be expected that there will be multiple dressing or sensor system changes. For example, wound dressing may be changed every few days, and a wound may take approximately 4 weeks to heal. Thus, it can be advantageous to determine how a wound dressing is positioned relative to the area of interest 670. For example, it can be advantageous to determine which sensors correspond to (for example, measure from) the area of interest 670.

The system can determine a position or orientation of the wound dressing, for example, relative to the wound 650 or the point of reference 660. For example, by tracking or determining where the wound dressing (or its sensors) are relative to the area of interest, the system can determine which sensors are proximate (for example, measuring from or relative to) the area of interest 670. The point of reference 660 can serve as a reference for determining a position or orientation of one or more sensors, a sensor package, a wound, or the like. For example, a system can determine the emplacement of the point of reference 660 or the emplacement of one or more sensors or the wound dressing relative to the point of reference 660. Based at least in part on the determined emplacement, the system can determine which sensors, if any, correspond to the area of interest 670. Accordingly, the system can monitor the area of interest 670 throughout the duration of healing by determining the position or orientation of the wound dressing or sensors.

Alignment Features

Figure 7:
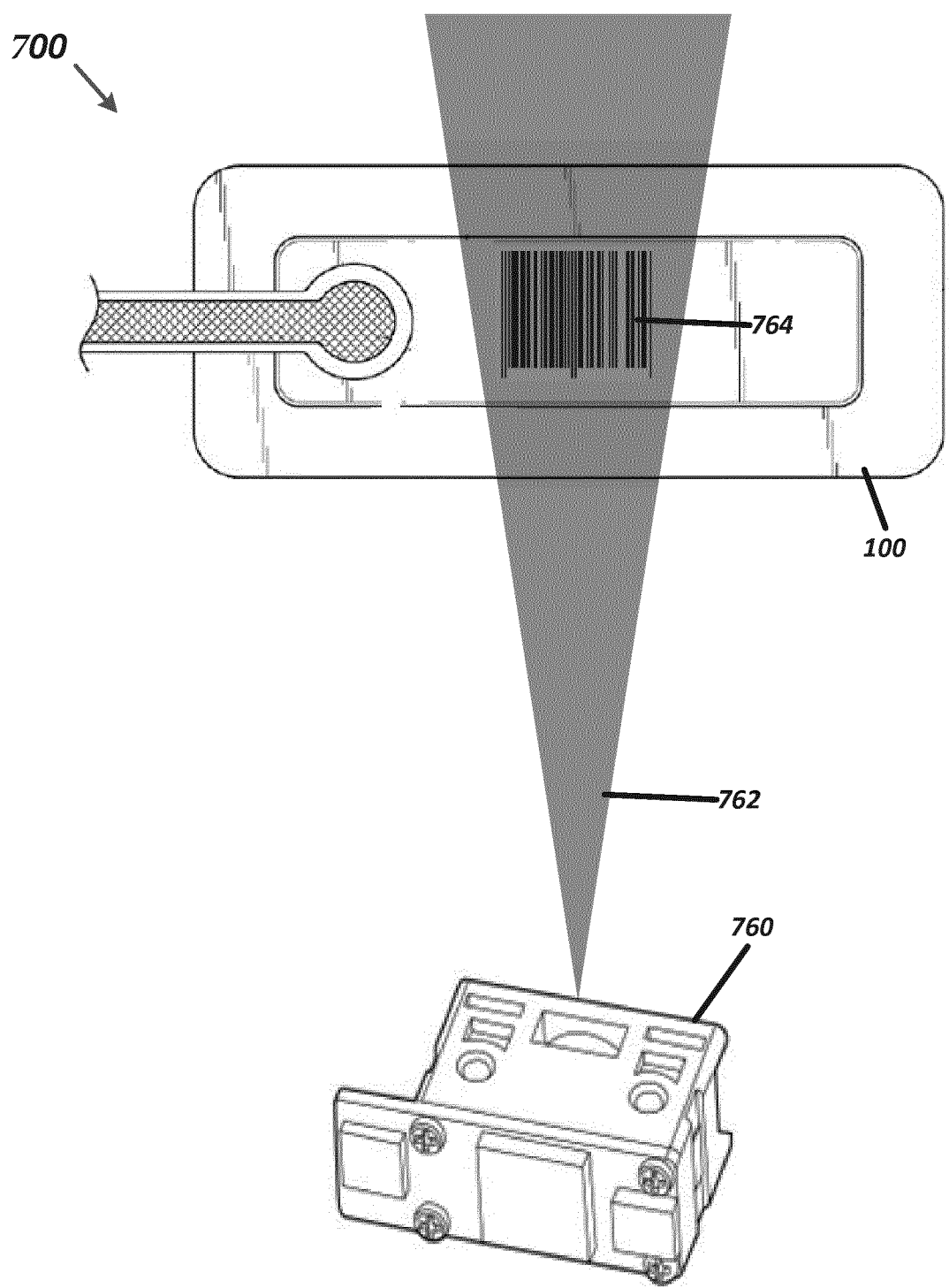
FIG. 7 illustrates a monitoring or therapy system utilizing pH-sensitive ink on a wound dressing according to some embodiments.

FIG. 7 illustrates a monitoring or therapy system 700 for determining a position or orientation of a wound dressing 100. The system can include a wound dressing 100 and a positioning sensing device 760. In some cases, the system 700 can be a NPWT system. As illustrated, an alignment feature 764 can be associated with the wound dressing 100. The position device 760 can be configured to determine a position or orientation of the wound dressing (or a wound, body part, etc.) based at least in part on the alignment feature 764.

The alignment feature 764 can include any of the alignment features described herein including, but not limited to, an alphanumeric or other code, a standard or irregular shape, or other discrete marking (for example, referred to as a baseline shape). For example, a starburst (such as the Smith & Nephew logo) could be utilized with a number included. In addition, any standard shape that has a known aspect ratio could be usable for the baseline shape. One or more alignment features 764 can be printed onto a surface of the wound dressing 100. However, it will be understood that the alignment feature 764 can be associated with the wound dressing 100 in various ways.

The positioning sensing device 760 (or associated processor) can determine a position or orientation of the wound dressing 100, a wound, or the like. For example, the positioning sensing device 760 can include an optical sensor (for example, a red, green, blue, and clear (RGBC) sensor or a red, green blue, and white (RGBW) sensor), camera or scanner, and the positioning sensing device 760 can read or determine characteristics of the alignment feature 764.

The positioning sensing device 760 can read, scan, or gather information from the alignment feature 764. For example, the positioning sensing device 760 can determine an angle of the alignment feature 764 or the dressing 100 relative to the positioning sensing device 760 or a beam 762 (such as, a scan beam). In addition or alternatively, the positioning sensing device 760 can determine a relative size of the elements in an image or video of the positioning sensing device 760. In addition or alternatively, the positioning sensing device 760 can determine a position of the alignment feature 764 on the wound dressing 100.

In some embodiments, one or more characteristics of the alignment feature 764 can be used to determine one or more other characteristics. For example, an angle of the alignment feature 764 relative to the positioning sensing device 760 can be identified based at least in part on the relative size of elements within an image or video of the positioning sensing device 760. For instance, the skew or parallax of the elements can be used to determine the angle.

The alignment feature 764 can be formed of or placed using various inks. For example, the alignment feature 764 can include pH-sensitive ink, such as, but not limited to, pH-sensitive dyes, pH-sensitive pigment, or the like. The pH-sensitive ink can be configured to change color, for example, based on a solution that comes into contact with the ink. Accordingly, in some cases, wound fluid can cause the ink to change to a particular color. Other substances, such as non-pH sensitive ink, can be utilized in addition to or in place of pH-sensitive ink. In some implementations, multiple markings can be used.

In some embodiments, the alignment feature 764 is used to determine a model of the wound dressing 100, such as a 3D map. For example, a 3D orientation of an alignment feature 764 can be identified by the perspective shortening of a known shape. A square may, for instance, appear as a trapezium if it is tilted away from the camera. Thus, in some embodiments, when a position, shape, orientation, or size of the alignment feature 764 is known, a location, an angle in three dimensions, or a distance of the alignment feature 764 from the positioning sensing device, the patient, or another object can be calculated. A 3D map of the dressing shape can therefore be generated by interpolating between the known points, such as the angle and position of the alignment feature 764. This 3D modeling can be used with alignment features 764 incorporating pH ink as well. For example, a 3D map can be determined from a position or color of a pH element.

In addition or alternatively, the alignment feature 764 can be utilized to determine a compression of the wound dressing 100. For example, a 3D orientation, angle, size, shape, or the like of an alignment feature 764 can be identified, and from this information, a compression of the wound dressing 100 can be determined. For example, a smaller shape, a particular angle, a broken shape, or the like and indicate that the wound dressing 100 is compressed.

In some embodiments, a pH sensor can be utilized to, for instance, measure, assess, or treat a wound. For example, in some embodiments, a pH-sensitive ink can be utilized to convert an optical sensor into a pH sensor. For example, the pH-sensitive ink can be incorporated into an adhesive substance, such as an adhesive foam or gel, to form a pH-sensitive adhesive substance which can be placed or printed onto an optical component, such as an optical sensor, of a sensing platform. A remaining portion of a sensing platform can be coated with a transparent or translucent adhesive.

By combining the pH-sensitive ink with the adhesive substance and generating a pH-sensitive adhesive substance, the pH-sensitive adhesive substance is effectively increasing the thickness of the pH-sensitive ink (as compared to the thickness of a layer of pH-sensitive ink itself). Accordingly, the pH-sensitive adhesive substance provides a greater color delta for a greater signal-to-noise ratio. Thus, almost any optical sensor can be turned into a pH sensor simply by printing a pH-doped adhesive over the optical sensor and utilizing a color response table.

The pH-sensitive ink can incorporated into adhesive foam using a variety of techniques. For example, the pH-sensitive ink can be added to a raw foaming material prior to mixing. Alternatively, adhesive foam can be soaked in pH-sensitive ink. Similarly, pH-sensitive ink can incorporated into adhesive gel using a variety of techniques. For example, the pH-sensitive ink can simply be mixed with the adhesive gel.

In some embodiments, pH changing pads can be used as a pH sensor which is configured to change color in response to pH alterations in the wound environment. The change in color can then be optically measured and assessed. For example, a spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, the pH sensor includes foam or other expanding material which can change spectral absorption depending on pH of the environment. Advantageously, the foam can be integrated into the wound dressing or wound packing material.

In some embodiments, the pH sensor may also have a built-in exudate channeling system configured to enable the pH sensor to channel the flow of exudate across a pH-sensitive region more effectively.

Terminology

In some cases, one or more sensors can be positioned at a particular location(s) on a substrate or layer. A marker, such as a color marker, can be included to guide the user which way the one or more sensors should be positioned in a wound.

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A wound monitoring and/or therapy system, comprising:
    a wound dressing configured to be positioned in contact with a wound, the wound dressing comprising a plurality of sensors configured to measure a plurality of wound characteristics; and
    a controller including one or more processors, the controller configured to communicate with at least some of the plurality of sensors and further configured to:
        receive emplacement data associated with a point of reference;
        determine a position and/or orientation of the point of reference relative to the wound based at least in part on the received emplacement data;
        determine a position and/or orientation in the wound of a first sensor of the plurality of sensors based at least in part on the determined position and/or orientation of the point of reference;
        compare the position and/or orientation of the first sensor with threshold emplacement data indicating correct position and/or orientation in the wound of the first sensor; and based at least on the comparison, provide an indication that the first sensor is correctly positioned in the wound.

2. The system of claim 1, wherein the first sensor includes at least one nanosensor, thermistor, conductivity sensor, Sp02 sensor, pH sensor, color sensor, optical sensor, impedance sensor, or electrode.

3. The system of claim 2, wherein the first sensor comprises the optical sensor, and wherein the optical sensor comprises at least one of a red, green, blue, and clear (RGBC) sensor or red, green blue, and white (RGBW) sensor.

4. The system of claim 3, further comprising an emplacement sensor configured to detect the emplacement data, wherein the emplacement sensor comprises at least one of an external video camera or radio frequency (RF) sensor.

5. The system of claim 3, further comprising an emplacement sensor configured to detect the emplacement data, wherein the emplacement sensor is embedded in the wound dressing.

6. The system of claim 1, wherein the first sensor comprises a sensor other than an emplacement sensor configured to detect the emplacement data.

7. The system of claim 1, wherein the first sensor comprises an emplacement sensor configured to detect the emplacement data.

8. The system of claim 1, wherein the point of reference corresponds to a position and/or orientation of an emplacement sensor configured to detect the emplacement data.

9. The system of claim 1, wherein the position and/or orientation of the point of reference corresponds to a location that is remote from the wound dressing.

10. The system of claim 1, wherein the controller is further configured to determine a position and/or orientation in the wound of a second sensor of the plurality of sensors based at least on the received emplacement data and a relationship between positions and/or orientations in the wound dressing and/or the wound of the first and second sensors.

11. The system of claim 10, wherein the relationship comprises at least known position and/or orientation offset between the first and second sensors.

12. The system of claim 1, wherein at least some of the plurality of sensors are configured to communicate and/or co-register with each other, and wherein the controller is configured to provide the indication further based on co-registration data.

13. The system of claim 1, wherein at least one of the plurality of sensors is configured with adjustable sensor settings, and wherein the adjustable sensor settings are configured to be adjusted based at least in part on the received emplacement data.

14. The system of claim 1, wherein the wound dressing is configured to communicate negative pressure to the wound.

15. A method of operating a wound monitoring and/or therapy system comprising a wound dressing including a plurality of sensors configured to measure a plurality of wound characteristics, the method comprising:
receiving emplacement data associated with at least one point of reference;
determining a position and/or orientation of a first sensor of a plurality of sensors based at least in part on the received emplacement data;
comparing the position and/or orientation of the first sensor with threshold emplacement data indicating a correct position and/or orientation of the first sensor; and
based at least in part on the comparison, providing an indication that the first sensor is correctly positioned in the wound,
wherein the method is performed by a controller of a wound monitoring and/or therapy system.

16. The method of claim 15, wherein the first sensor includes at least one nanosensor, thermistor, conductivity sensor, Sp02 sensor, pH sensor, color sensor, optical sensor, impedances sensor, emplacement sensor configured to detect the emplacement data, or electrode.

17. The method of claim 15, wherein the first sensor comprises a sensor other than an emplacement sensor.

18. The method of claim 15, wherein the first sensor comprises an emplacement sensor configured to detect the emplacement data.

19. The method of claim 15, wherein the position and/or orientation of the point of reference corresponds to a position and/or orientation of an emplacement sensor configured to detect the emplacement data.

20. A wound monitoring and/or therapy system, comprising:
a wound dressing configured to be positioned in contact with a wound, the wound dressing comprising a plurality of sensors configured to measure a plurality of wound characteristics and at least one alignment feature is associated with a position and/or orientation of the wound dressing;
a positioning sensing device comprising a sensor and a controller including one or more processors, the controller configured to communicate with the sensor and further configured to:
based at least in part on data received from the sensor, determine a position and/or orientation of the at least one alignment feature;
based at least in part on the determined position and/or orientation of the at least one alignment feature, determine a position and/or orientation of at least one sensor of the plurality of sensors of the wound dressing; and
provide an indication of a status of the position and/or orientation of the at least one sensor relative to the wound.

* * * * *

UNITED STATES PATENT AND TRADEMARK OFFICE
CERTIFICATE OF CORRECTION

PATENT NO. : 11,633,153 B2
APPLICATION NO. : 16/625279
DATED : April 25, 2023
INVENTOR(S) : Varuni Rachindra Brownhill et al.

It is certified that error appears in the above-identified patent and that said Letters Patent is hereby corrected as shown below:

On the Title Page

On Page 3, Column 1, Line 14, under Item (56) U.S. Patent Documents, delete "Berne," and insert --Berner,--.

On Page 4, Column 1, Line 15, under Item (56) U.S. Patent Documents, delete "2018/0000817" and insert --2018/0008177--.

On Page 4, Column 2, Line 1, under Item (56) Foreign Patent Documents, delete "WO-20009052607" and insert --WO-2009052607--.

In the Specification

In Column 3, Line 7, delete "Sp02" and insert --SpO2--.

In Column 3, Line 10, delete "green" and insert --green,--.

In Column 4, Line 2, delete "Sp02" and insert --SpO2--.

In Column 5, Line 53, delete "Sp02" and insert --SpO2--.

In Column 5, Line 56, delete "green" and insert --green,--.

In Column 7, Line 19, delete "Sp02" and insert --SpO2--.

In Column 8, Line 6, delete "Sp02" and insert --SpO2--.

In Column 23, Line 49, delete "Renays" and insert --Renasys--.

In Column 27, Line 41, delete "In a" and insert --In--.

Signed and Sealed this
Twenty-ninth Day of August, 2023

Katherine Kelly Vidal
*Director of the United States Patent and Trademark Office*

CERTIFICATE OF CORRECTION (continued)
U.S. Pat. No. 11,633,153 B2

In Column 28, Line 44, delete "is can" and insert --can--.

In Column 33, Line 38, delete "fascitis." and insert --fasciitis.--.

In Column 36, Line 45, delete "fluropolymers" and insert --fluoropolymers--.

In Column 38, Line 65, delete "green" and insert --green,--.

In Column 39, Line 40, delete "Autoflourescense" and insert --Autofluorescence--.

In Column 40, Line 21, delete "10 kΩ," and insert --10 kQ,--.

In Column 45, Line 34, delete "user" and insert --user.--.

In Column 48, Line 53, delete "the" and insert --the one--.

In Column 52, Line 51, delete "green" and insert --green,--.

In the Claims

In Column 57, Line 6, Claim 2, delete "Sp02" and insert --SpO2--.

In Column 57, Line 11, Claim 3, delete "green" and insert --green,--.

In Column 58, Line 20, Claim 16, delete "Sp02" and insert --SpO2--.